(12) United States Patent
Nawa et al.

(10) Patent No.: US 6,691,582 B1
(45) Date of Patent: Feb. 17, 2004

(54) GAS TYPE IDENTIFICATION SYSTEM

(75) Inventors: Motoyuki Nawa, Ikoma (JP); Yukio Nagaoka, Soraku-gun (JP); Mitsuo Nanba, Machida (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/786,925

(22) PCT Filed: Sep. 10, 1999

(86) PCT No.: PCT/JP99/04971

§ 371 (c)(1),
(2), (4) Date: Aug. 1, 2001

(87) PCT Pub. No.: WO00/16090

PCT Pub. Date: Mar. 23, 2000

(30) Foreign Application Priority Data

Sep. 11, 1998 (JP) ............................................. 10-258136

(51) Int. Cl.[7] .................................................. G01F 1/66
(52) U.S. Cl. ................................................... 73/861.28
(58) Field of Search ............................. 73/861.28, 861, 73/23.2, 24.01; 137/78.4, 79

(56) References Cited

U.S. PATENT DOCUMENTS

| | | | | | |
|---|---|---|---|---|---|
| 4,596,133 | A | * | 6/1986 | Smalling et al. | ............ 73/24.01 |
| 5,060,514 | A | * | 10/1991 | Aylsworth | ................. 73/24.01 |
| 5,635,626 | A | * | 6/1997 | Hammond et al. | ........... 73/861 |
| 6,170,509 | B1 | * | 1/2001 | Karta | ........................ 137/78.4 |
| 6,279,378 | B1 | * | 8/2001 | Sheen et al. | ............... 73/24.01 |

FOREIGN PATENT DOCUMENTS

| EP | 0 572 581 B1 | 1/1997 |
|---|---|---|
| JP | 198688 | 8/1995 |

OTHER PUBLICATIONS

WO 93/13414—English Equivalent for JP 6–507725.*

* cited by examiner

*Primary Examiner*—Harshad Patel
(74) *Attorney, Agent, or Firm*—Snell & Wilmer, LLP

(57) ABSTRACT

A gas type identification system includes: a flow path; an ultrasonic measurement section disposed in the flow path, the ultrasonic measurement section including a pair of ultrasonic transducers; a sound velocity calculation section for calculating a sound velocity of a gas flowing through the flow path based on a signal from the ultrasonic measurement section; a sound velocity memory section for previously storing a predetermined sound velocity; and a comparison section for comparing the sound velocity calculated by the sound velocity calculation section with the predetermined sound velocity previously stored in the sound velocity memory section.

16 Claims, 23 Drawing Sheets

GAS TYPE IDENTIFICATION SYSTEM

TECHNICAL FIELD

The present invention relates to a gas type identification system for identifying the type of gas that flows in a flow path and automatically setting conditions which are suitable for that gas type.

BACKGROUND ART

Conventionally, methods are known for utilizing the sound velocity of a gas in a flow rate measurement apparatus for diagnosing the malfunctioning of a flow rate meter. Such a method is described in, for example, Japanese Laid-Open Publication No. 8-304135.

FIG. 1 shows the structure of a flow rate measurement apparatus described in Japanese Laid-Open Publication No. 8-304135.

As shown in FIG. 1, the flow rate measurement apparatus includes an ultrasonic measurement section 1, a sound velocity calculation section 2, a sound velocity setting section 3, a temperature measurement section 4, a sound velocity calculation section 5, and a comparison section 6.

The sound velocity calculation section 2 calculates a sound velocity based on a signal which is output from the ultrasonic measurement section 1. The sound velocity which has been calculated by the sound velocity calculation section 2 is output to the comparison section 6. Based on a temperature signal which is output from the temperature measurement section 4, the sound velocity calculation section 5 performs temperature compensation for a sound velocity which is previously set in the sound velocity setting section 3. The sound velocity which has been subjected to temperature compensation by the sound velocity calculation section 5 is output to the comparison section 6. The comparison section 6 compares the sound velocity which is output from the sound velocity calculation section 2 with the sound velocity which is output from the sound velocity calculation section 5. Based on the comparison result by the comparison section 6, it is determined whether the ultrasonic measurement section 1 is malfunctioning or not.

Thus, conventional systems diagnoses whether or not a flow rate measurement apparatus is malfunctioning under the premise that the type of gas is known. Conventional systems do not identify gas types. Conventional systems do not set conditions according to gas types.

DISCLOSURE OF THE INVENTION

A gas type identification system according to the present invention includes: a flow path; an ultrasonic measurement section disposed in the flow path, the ultrasonic measurement section including a pair of ultrasonic transducers; a sound velocity calculation section for calculating a sound velocity of a gas flowing through the flow path based on a signal from the ultrasonic measurement section; a sound velocity memory section for previously storing a predetermined sound velocity; and a comparison section for comparing the sound velocity calculated by the sound velocity calculation section with the predetermined sound velocity previously stored in the sound velocity memory section.

In one embodiment of the invention, the gas type identification system further includes: a flow rate compensation coefficient setting section for setting a flow rate compensation coefficient in accordance with a result of the comparison by the comparison section; and a flow rate calculation section for calculating a flow rate of the gas flowing through the flow path based on the signal from the ultrasonic measurement section and the flow rate compensation coefficient.

In another embodiment of the invention, the gas type identification system further includes: a dual mode valve disposed in the flow path; and a control section for controlling the dual mode valve in accordance with a result of the comparison by the comparison section.

In still another embodiment of the invention, the gas type identification system further includes: a dual mode valve disposed in the flow path; a safety standards setting section for setting safety standards in accordance with a result of the comparison by the comparison section; a determination section for determining whether or not the safety standards are satisfied; and a control section for controlling the dual mode valve in accordance with a result of the determination by the determination section.

Alternatively, the gas type identification system according to the present invention includes: a flow path; a temperature measurement section disposed in the flow path; a temperature calculation section for calculating a temperature of a gas flowing through the flow path based on a signal from the temperature measurement section; an ultrasonic measurement section disposed in the flow path, the ultrasonic measurement section including a pair of ultrasonic transducers; a sound velocity calculation section for calculating a sound velocity of the gas flowing through the flow path based on a signal from the ultrasonic measurement section; a temperature/sound velocity memory section for previously storing a predetermined temperature and a predetermined sound velocity; and a comparison section for comparing the temperature calculated by the temperature calculation section with the predetermined temperature previously stored in the temperature/sound velocity memory section and comparing the sound velocity calculated by the sound velocity calculation section with the predetermined sound velocity previously stored in the temperature/sound velocity memory section.

In one embodiment of the invention, the gas type identification system further includes: a flow rate compensation coefficient setting section for setting a flow rate compensation coefficient in accordance with a result of the comparison by the comparison section; and a flow rate calculation section for calculating a flow rate of the gas flowing through the flow path based on the signal from the ultrasonic measurement section and the flow rate compensation coefficient.

In another embodiment of the invention, the gas type identification system further includes: a dual mode valve disposed in the flow path; and a control section for controlling the dual mode valve in accordance with a result of the comparison by the comparison section.

In still another embodiment of the invention, the gas type identification system further includes: a dual mode valve disposed in the flow path; a safety standards setting section for setting safety standards in accordance with a result of the comparison by the comparison section; a determination section for determining whether or not the safety standards are satisfied; and a control section for controlling the dual mode valve in accordance with a result of the determination by the determination section.

Alternatively, the gas type identification system according to the present invention includes: a flow path; a temperature measurement section disposed in the flow path; a temperature calculation section for calculating a first temperature and a second temperature of a gas flowing through the flow path based on a signal from the temperature measurement section; an ultrasonic measurement section disposed in the flow path, the ultrasonic measurement section including a pair of ultrasonic transducers; a sound velocity calculation section for calculating a first sound velocity and a second sound velocity of the gas flowing through the flow path based on a signal from the ultrasonic measurement section; a temperature/sound velocity memory section for previously storing a predetermined temperature and a predetermined sound velocity; and a comparison section for comparing the first temperature and the second temperature calculated by the temperature calculation section with the predetermined temperature previously stored in the temperature/sound velocity memory section and comparing the first sound velocity and the second sound velocity calculated by the sound velocity calculation section with the predetermined sound velocity previously stored in the temperature/sound velocity memory section.

In one embodiment of the invention, the gas type identification system further includes: a flow rate compensation coefficient setting section for setting a flow rate compensation coefficient in accordance with a result of the comparison by the comparison section; and a flow rate calculation section for calculating a flow rate of the gas flowing through the flow path based on the signal from the ultrasonic measurement section and the flow rate compensation coefficient.

In another embodiment of the invention, the gas type identification system further includes: a dual mode valve disposed in the flow path; and a control section for controlling the dual mode valve in accordance with a result of the comparison by the comparison section.

In still another embodiment of the invention, the gas type identification system further includes: a dual mode valve disposed in the flow path; a safety standards setting section for setting safety standards in accordance with a result of the comparison by the comparison section; a determination section for determining whether or not the safety standards are satisfied; and a control section for controlling the dual mode valve in accordance with a result of the determination by the determination section.

Thus, the invention described herein makes possible the advantage of providing a gas type identification system which identifies the type of gas that flows in a flow path and automatically sets conditions which are suitable for that gas type.

BEST MODE FOR CARRYING OUT THE INVENTION

Hereinafter, examples of the present invention will be described with reference to the figures.

EXAMPLE 1

Figure 1:
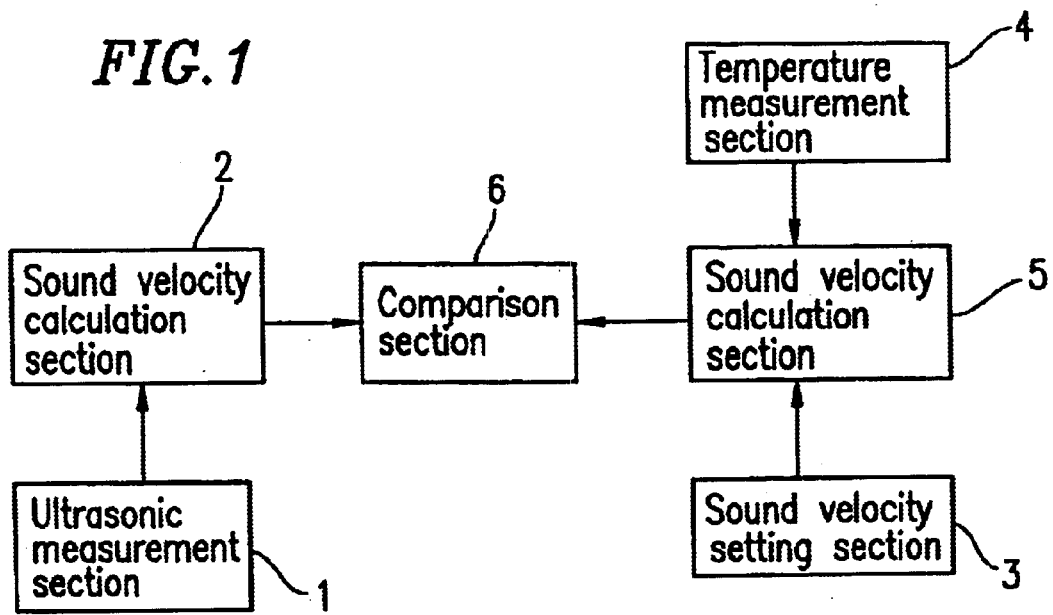
FIG. 1 is a block diagram showing the structure of a conventional malfunctioning diagnosis system utilizing sound velocity.
Figure 2:
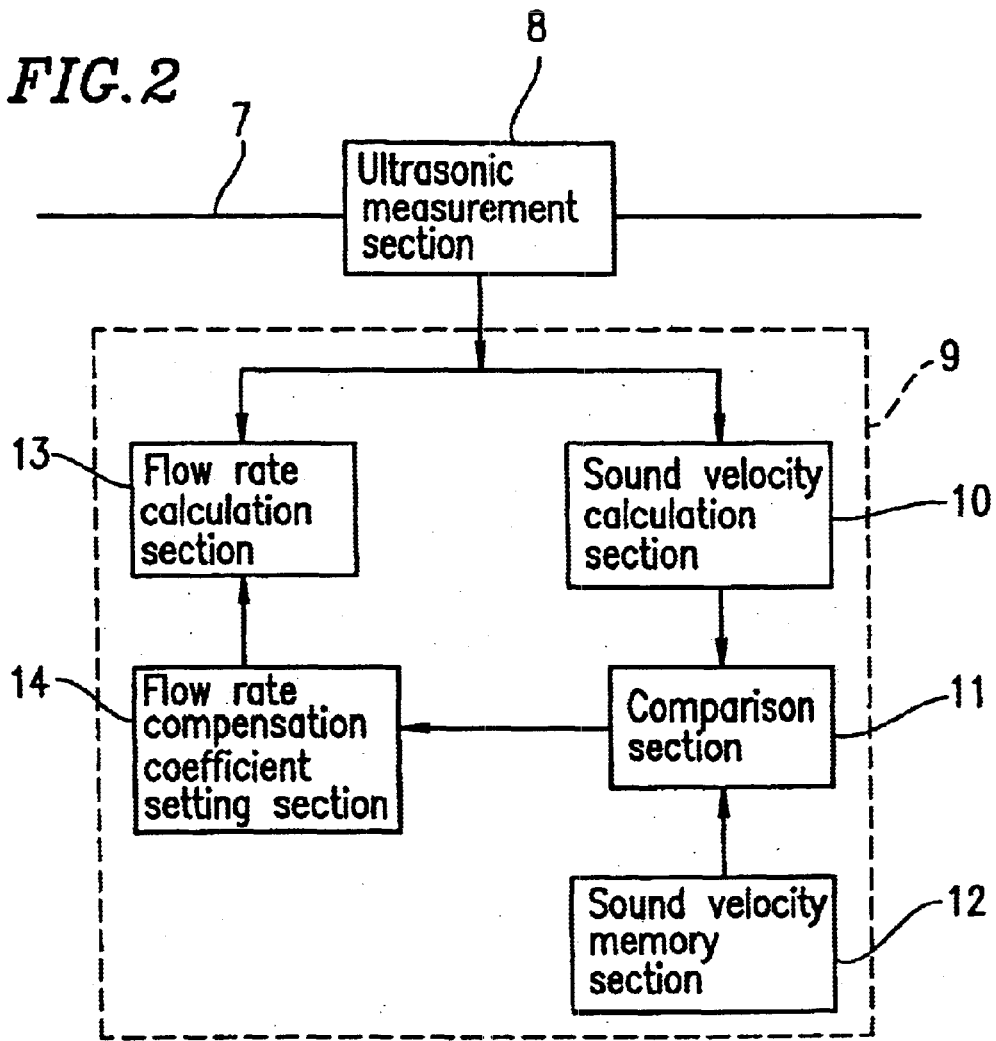
FIG. 2 is a block diagram showing the structure of a gas type identification system according to Example 1 of the present invention.

FIG. 2 shows the structure of a gas type identification system according to Example 1 of the present invention. As shown in FIG. 2, the gas type identification system includes a flow path 7, an ultrasonic measurement section 8 disposed in the flow path 7, and a calculation section 9 for performing a mathematical operation for a signal which is output from the ultrasonic measurement section 8.

The calculation section 9 includes a sound velocity calculation section 10, a comparison section 11, a sound velocity memory section 12, a flow rate calculation section 13, and a flow rate compensation coefficient setting section 14.

Next, the operation and functions of the gas type identification system will be described.

The sound velocity calculation section 10 calculates a sound velocity based on a signal which is output from the ultrasonic measurement section 8. The comparison section 11 compares the sound velocity which has been calculated by the sound velocity calculation section 10 with a sound velocity(s) which is previously stored in the sound velocity memory section 12. The type of gas is identified based on the result of the comparison by the comparison section 11. A flow rate compensation coefficient which corresponds to the identified gas type is set by the flow rate compensation coefficient setting section 14. The flow rate calculation section 13 calculates a flow rate based on a signal which is output from the ultrasonic measurement section 8 by using the flow rate compensation coefficient which has been set by the flow rate compensation coefficient setting section 14.

Figure 3:
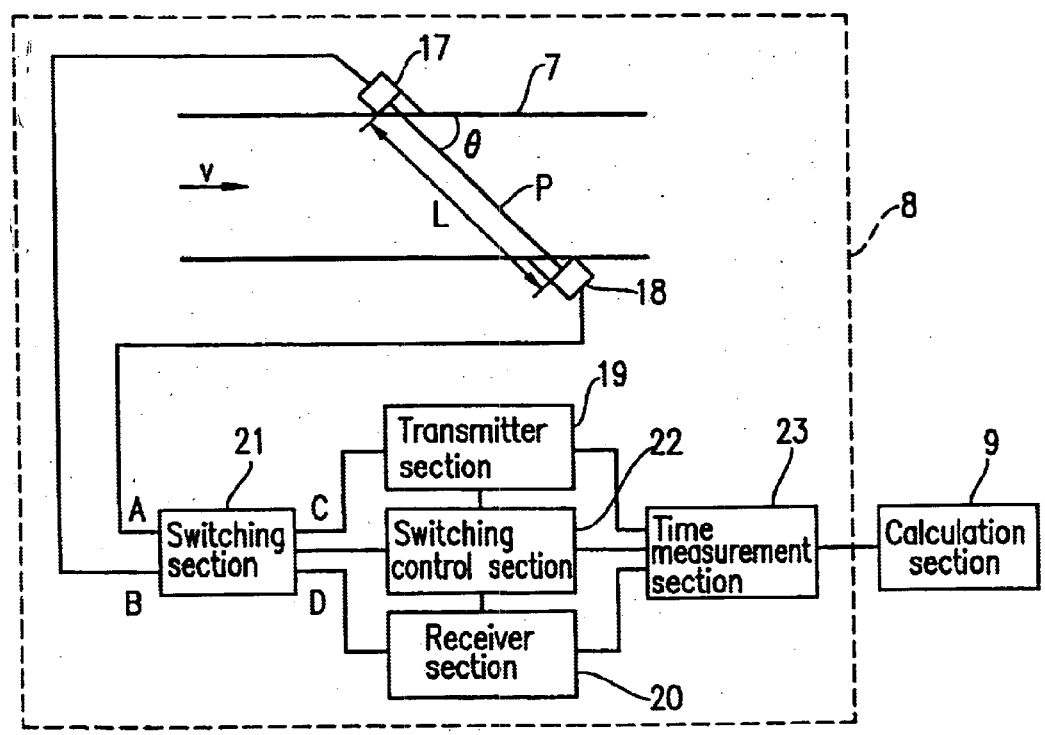
FIG. 3 is a block diagram showing the structure of an ultrasonic measurement section in a gas type identification system.

FIG. 3 shows the structure of the ultrasonic measurement section 8 shown in FIG. 2.

The ultrasonic measurement section 8 includes a pair of ultrasonic transducers 17 and 18, a transmitter section 19, a receiver section 20, a switching section 21, a switching control section 22, and a time measurement section 23.

Next, the ultrasonic measurement section 8 will be described in detail with reference to FIG. 3.

First, a method for measuring the flow rate of a gas which flows through the flow path 7 will be described. The switching section 21 includes terminals A to D. The interconnection between terminals A to D in the switching section 21 can be switched by means of the switching control section 22.

First, terminal B of the switching section 21 is coupled to terminal C, and terminal A of the switching section 21 is coupled to terminal D. In this case, a signal which has been transmitted from the transmitter section 19 will be input to the ultrasonic transducer 17 via terminals C and B of the switching section 21. The ultrasonic waves which are output from the ultrasonic transducer 17 travel across the flow path 7 so as to reach the ultrasonic transducer 18. A signal which is output from the ultrasonic transducer 18 is received by the receiver section 20 via terminals A and D of the switching section 21.

The transmitter section 19 transmits a signal to the ultrasonic transducer 17 via the switching section 21, and simultaneously outputs that signal to the time measurement section 23. The receiver section 20 receives the signal from the ultrasonic transducer 18 via the switching section 21, and simultaneously outputs the received signal to the time measurement section 23. The time difference between these signals is measured by the time measurement section 23. As a result, the amount of time (T1) which elapses while the ultrasonic waves which have been output from the ultrasonic transducer 17 travel across the flow path 7 to reach the ultrasonic transducer 18 is obtained.

Next, the interconnection between terminals A to D in the switching section 21 is changed so that terminal A of the switching section 21 is coupled to terminal C, and terminal B of the switching section 21 is coupled to terminal D. As a result, the amount of time (T2) which elapses while the ultrasonic waves which have been output from the ultrasonic transducer 18 travel across the flow path 7 to reach the ultrasonic transducer 17 is obtained.

The flow rate of the gas which flows through the flow path 7 can be calculated in accordance with the following formulae, by using the time amounts T1 and T2 measured in the aforementioned manner.

Herein, it is assumed that the flow of the gas to be measured and the ultrasonic wave propagation path P constitute an angle θ; the ultrasonic transducer 17 and the ultrasonic transducer 18 are apart by a distance of L; and the gas has a sound velocity of c.

The time amounts T1 and T2 can be calculated in accordance with eq. (1) and eq. (2):

$$T1=L/(c+v(\cos \theta)) \quad (1)$$

$$T2=L/(c-v(\cos \theta)) \quad (2)$$

By eliminating the sound velocity c from eq. (1) and (2), a flow velocity v can be calculated in accordance with eq. (3):

$$v=(L/2\cos \theta)((1/T1)-(1/T2)) \quad (3)$$

The flow rate Q can be calculated in accordance with eq. (4):

$$Q=kvS \quad (4)$$

In eq. (4), k represents a compensation coefficient for deriving an average flow velocity, and S represents the cross-sectional area of the flow path 7. Herein, k will be referred to as the "flow rate compensation coefficient".

By eliminating the flow velocity v from eq. (1) and (2), the sound velocity c can be calculated in accordance with eq. (5):

$$c=(L/2\cos \theta)((1/T1)+(1/T2)) \quad (5)$$

Although a method described herein derives the time amounts T1 and T2 by one measurement for each, i.e., by transmitting ultrasonic waves from the upstream side of the flow path 7 to the downstream aide and transmitting ultrasonic waves from the downstream side of the flow path 7 to the upstream side, a so-called "sing around" method may be adopted which repeatedly performs multiple time measurements during transmission/reception for improved measurement accuracy. In this case, mean values of a plurality of measured time amounts may be adopted as the time amounts T1 and T2.

Figure 4:
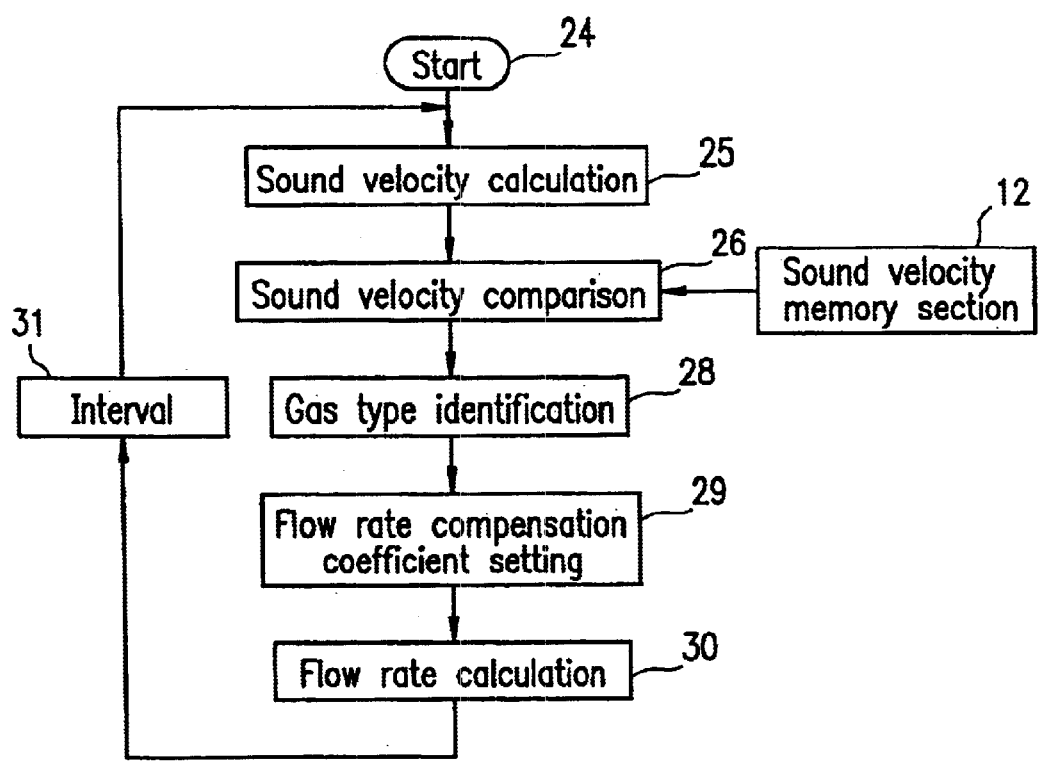
FIG. 4 is a flowchart showing the procedure to be performed by a calculation section in a gas type identification system.

FIG. 4 shows the procedure to be performed by the calculation section 9 shown in FIGS. 2 and 3.

In FIG. 4, reference numeral 24 denotes a start command; 25 denotes a sound velocity calculation command; 26 denotes a sound velocity comparison command; 28 denotes a gas type identification command; 29 denotes a flow rate compensation coefficient setting command; 30 denotes a flow rate calculation command; and 31 denotes an interval setting command.

The sound velocity calculation command 25 corresponds to the sound velocity calculation section 10 (FIG. 2); the sound velocity comparison command 26 corresponds to comparison section 11 (FIG. 2); the flow rate compensation coefficient setting command 29 corresponds to the flow rate compensation coefficient setting section 14 (FIG. 2); and the flow rate calculation command 30 corresponds to the flow rate calculation section 13 (FIG. 2).

As shown in FIG. 4, the program is begun responsive to the start command 24. Responsive to the sound velocity calculation command 25, the sound velocity of the gas which flown through the flow path 7 is calculated in accordance with eq. (5). Next, responsive to the sound velocity comparison command 26, the various sound velocity values which are previously stored in the sound velocity memory section 12 are compared with the sound velocity value which has been calculated responsive to the sound velocity calculation command 25. Responsive to the gas type identification command 28, the type of gas is identified based on the result of the comparison by the sound velocity comparison command 26.

Responsive to the flow rate compensation coefficient setting command 29, a flow rate compensation coefficient which corresponds to the identified gas type is set. Responsive to the flow rate calculation command 30, a flow rate which corresponds to the identified gas type is calculated in accordance with eq. (4), by using the flow velocity v which has been calculated in accordance with eq. (3) and the flow rate compensation coefficient k which has been set responsive to the flow rate compensation coefficient setting command 29.

The above process is repeated after the lapse of an amount of time which is set by an interval setting command 31. In this process, if the gas type is changed, a flow rate corresponding to the gas type after the change will be calculated.

Figure 5:
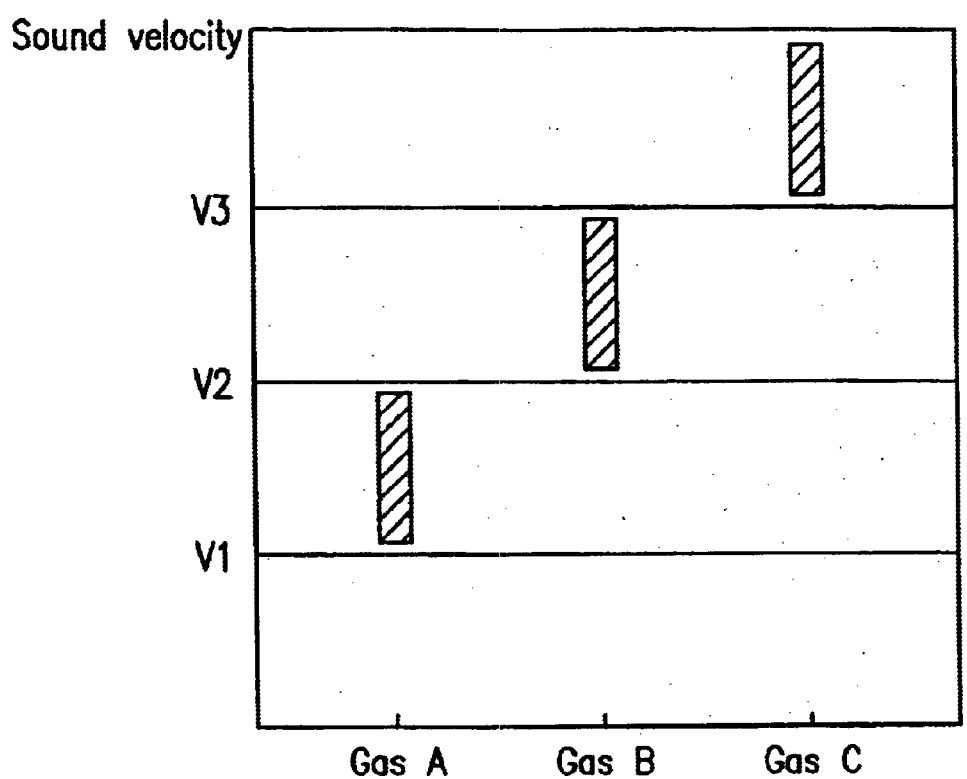
FIG. 5 is a graph showing the relationship between gas types and sound velocities.

FIG. 5 shows the relationship between gas types and sound velocities. Some gases have ranges of sound velocities which are clearly distinguishable from one another depending on their types. For example, gas A, gas B, and gas C shown in FIG. 5 can be clearly distinguished by calculating their sound velocities. The relationship between gas types and sound velocity ranges can be retained in the form of some formulae or a table. In the present example, such relationship is stored in the sound velocity memory section 12.

For example, if the sound velocity a which has been calculated responsive to the sound velocity calculation command 25 satisfies the following formula, then the gas flowing through the flow path 7 is identified as gas A:

$V1 < c < V2.$

Figure 6:
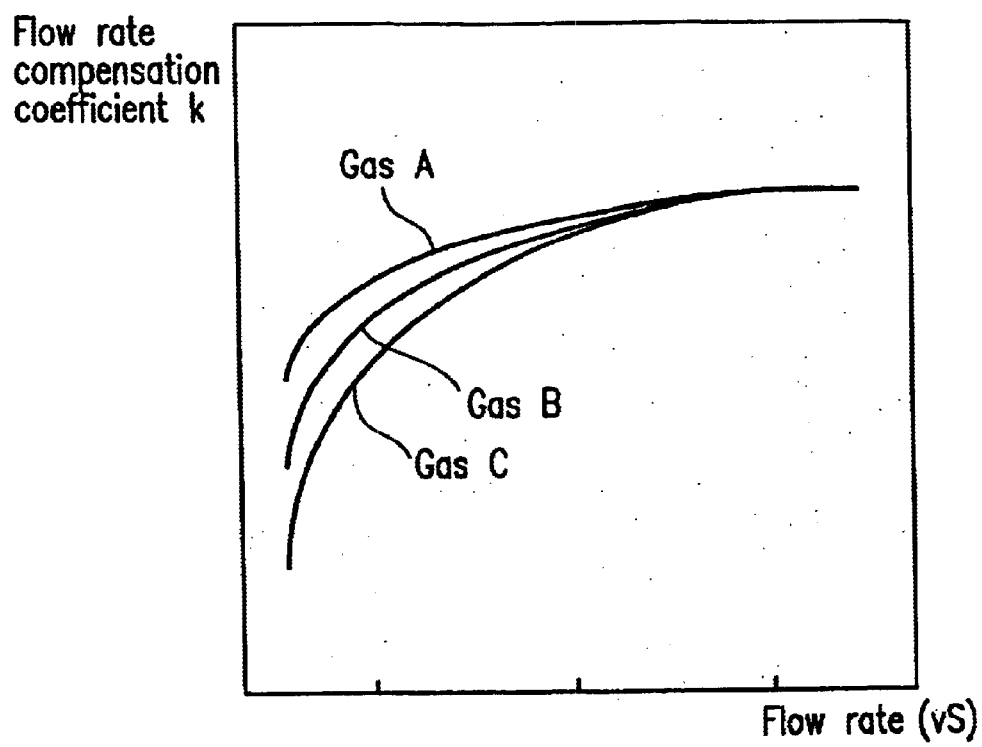
FIG. 6 is a graph showing the relationship between gas types and flow rate compensation coefficients.

FIG. 6 shows the relationship between gas types and flow rate compensation coefficients.

Different gas types may have different flow velocity distribution for the same flow rate due to differences in the physicochemical properties of the gases. As shown in FIG. 6, the flow rate compensation coefficient k for a given flow rate (vS), which is a product of the measured flow velocity v and the cross-sectional area S, may differ depending on the gas type.

As described above, by identifying the gas type based on sound velocity calculation, it is possible to calculate a flow rate which corresponds to the gas type. As a result, it is possible to make various settings according to gas types. For example, since city gas, air, propane gas have respectively different sound velocity ranges, it is possible to determine these gas types in accordance with the aforementioned method and calculate the flow rates corresponding to such gas types. By constructing a gas meter having such a structure, it is possible to realize a universal gas meter which is indifferent to gas types.

EXAMPLE 2

Figure 7:
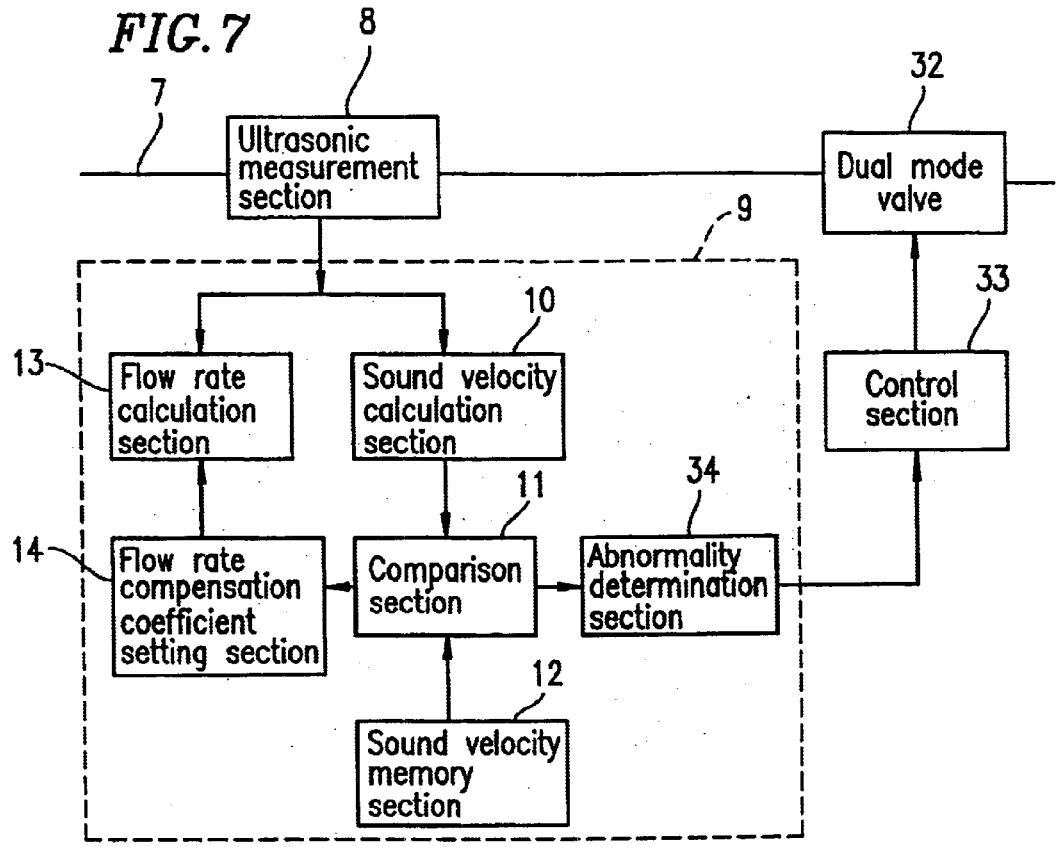
FIG. 7 is a block diagram showing the structure of a gas type identification system according to Example 2 of the present invention.

FIG. 7 shows the structure of a gas type identification system according to Example 2 of the present invention.

As shown in FIG. 7, the gas type identification system includes a flow path 7, an ultrasonic measurement section 8 disposed in the flow path 7, a calculation section 9 for performing a mathematical operation for a signal which is output from the ultrasonic measurement section 8, a dual mode valve 32 disposed in the flow path 7, and a control section 33 for controlling the dual mode valve 32. The dual mode valve 32 is disposed downstream from the ultrasonic measurement section 8 in the flow path 7.

In addition to the structure shown in FIG. 2, the calculation section 9 further includes an abnormality determination section 34. The abnormality determination section 34 determines whether or not an abnormal gas is flowing through the flow path 7. For example, if the gas type which is expected to flow through the flow path 7 (e.g., gas type A) is different from the gas type which actually flows through the flow path 7 (e.g., gas type B), then the abnormality determination section 34 determines that "an abnormal gas is flowing through the flow path 7". The gas type which is expected to flow through the flow path 7 is, for example, retained in the abnormality determination section 34. The gas type which actually flows through the flow path 7 is identified based on the result of the comparison by the comparison section 11.

In Example 2, the same constituent elements as those in Example 1 are indicated by like reference numerals, and the descriptions thereof are omitted.

Figure 8:
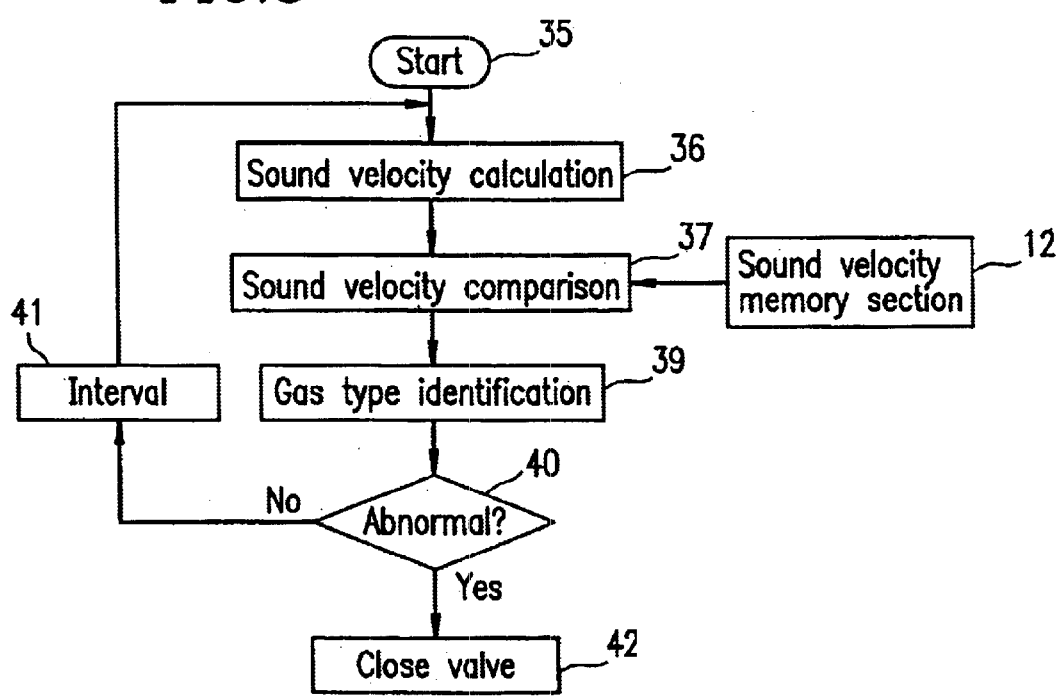
FIG. 8 is a flowchart showing the procedure to be performed by a calculation section in a gas type identification system.

FIG. 8 shows the procedure to be performed by the calculation section 9.

In FIG. 8, reference numeral 35 denotes a start command; 36 denotes a sound velocity calculation command; 37 denotes a sound velocity comparison command; 39 denotes a gas type identification command; 40 denotes an abnormality determination command; 41 denotes an interval setting command; and 42 denotes a valve closing command.

Now, it is assumed that gas B is actually flowing through the flow path 7 instead of gas A, which is expected to be flowing through the flow path 7.

As shown in FIG. 8, the program is begun responsive to the start command 35. Responsive to the sound velocity calculation command 36, the sound velocity of the gas which flows through the flow path 7 is calculated in accordance with eq. (5). Next, responsive to the sound velocity comparison command 37, the various sound velocity values which are previously stored in the sound velocity memory section 12 are compared with the sound velocity value which has been calculated responsive to the sound velocity calculation command 36. Responsive to the gas type identification command 39, the type of gas is identified based on the result of the comparison by the sound velocity comparison command 37.

For example, if the sound velocity c which has been calculated responsive to the sound velocity calculation command 36 satisfies the following formula, then the gas flowing through the flow path 7 is identified as gas B:

$V2 < c < V3.$

In this case, since gas B has flowed through the flow path 7 instead of gas A, it is determined that "an abnormal gas is flowing through the flow path 7" responsive to the abnormality determination command 40, and the valve closing command 42 is executed. As a result, the dual mode valve 32 is closed.

If the gas flowing through the flow path 7 is identified as gas A, it is determined that "a normal gas is flowing through the flow path 7" responsive to the abnormality determination command 40. After the lapse of an amount of time which is set by the interval setting command 41, the above process is repeated.

As described above, by identifying the gas type based on sound velocity calculation, it is possible to immediately shut off the flow of any gas that is not the specified gas, thereby providing for safety.

EXAMPLE 3

Figure 9:
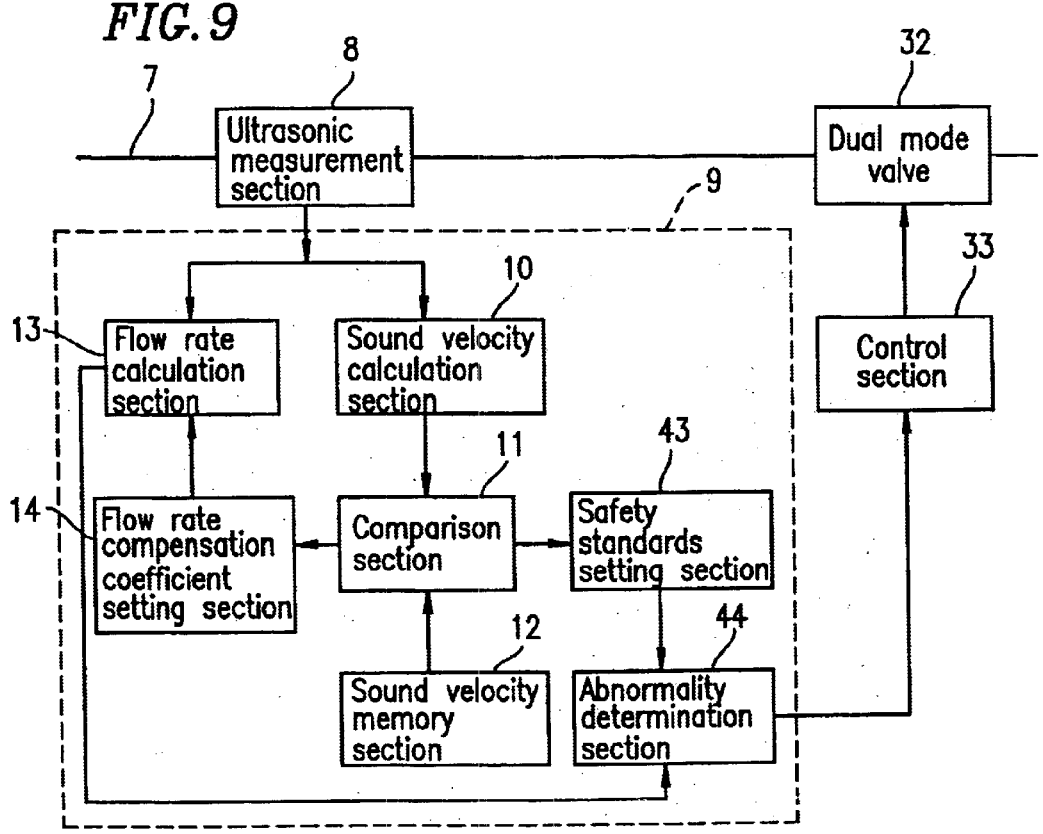
FIG. 9 is a block diagram showing the structure of a gas type identification system according to Example 3 of the present invention.

FIG. 9 shows the structure of a gas type identification system according to Example 3 of the present invention.

As shown in FIG. 9, the gas type identification system includes a flow path 7, an ultrasonic measurement section 8 disposed in the flow path 7, a calculation section 9 for performing a mathematical operation for a signal which is output from the ultrasonic measurement section 8, a dual mode valve 32 disposed in the flow path 7, and a control section 33 for controlling the dual mode valve 32. The dual mode valve 32 is disposed downstream from the ultrasonic measurement section 8 in the flow path 7.

In addition to the structure shown in FIG. 2, the calculation section 9 further includes a safety standards setting section 43 and an abnormality determination section 44.

In Example 3, the same constituent elements as those in Example 1 are indicated by like reference numerals, and the descriptions thereof are omitted.

Figure 10:
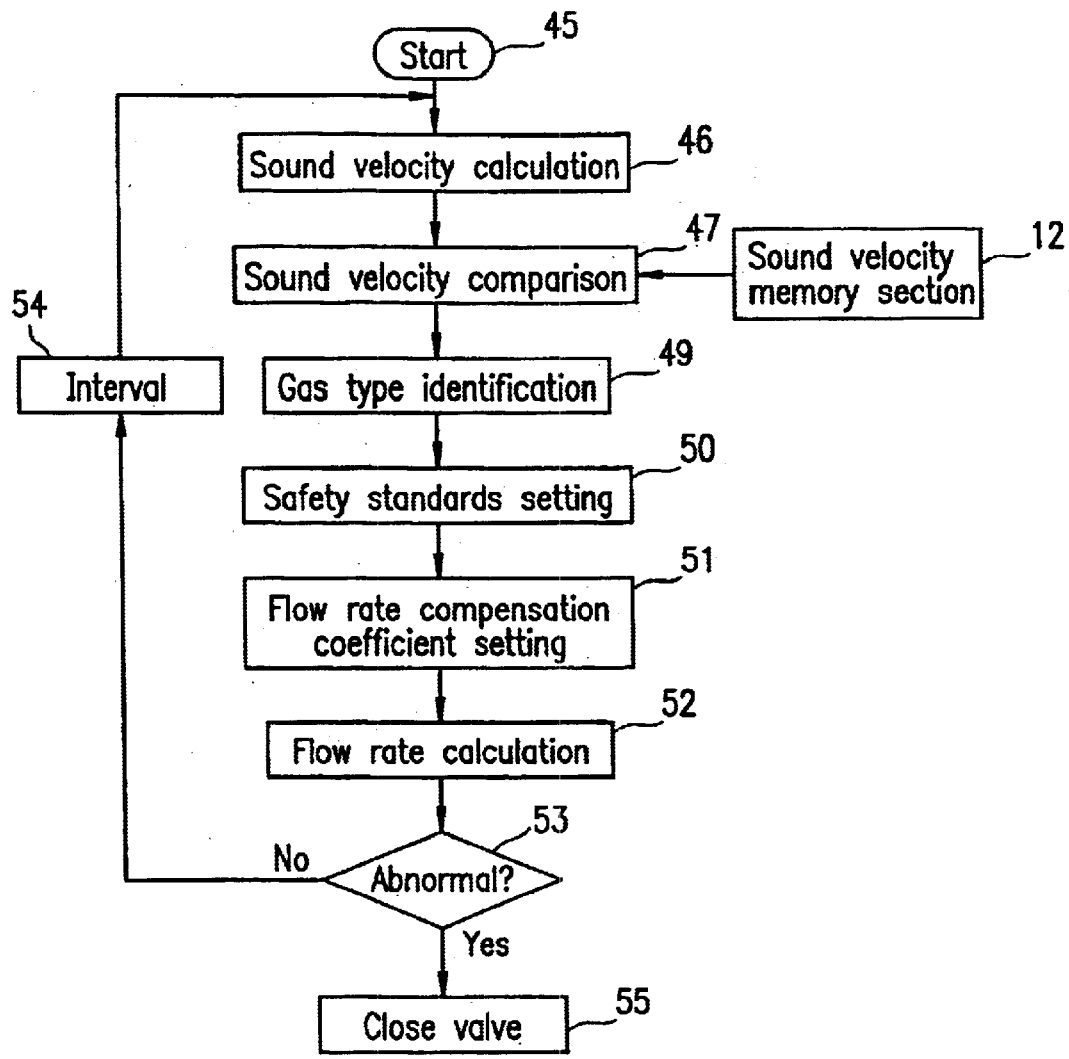
FIG. 10 is a flowchart showing the procedure to be performed by a calculation section in a gas type identification system.

FIG. 10 shows the procedure to be performed by the calculation section 9.

In FIG. 10, reference numeral 45 denotes a start command; 46 denotes a sound velocity calculation command; 47 denotes a sound velocity comparison command; 49 denotes a gas type identification command; 50 denotes a safety standards setting command; 51 denotes a flow rate compensation coefficient setting command; 52 denotes a flow rate calculation command; 53 denotes an abnormality determination command; 54 denotes an interval setting command; and 55 denotes a valve closing command.

The safety standards setting command 50 corresponds to the safety standards setting section 43 (FIG. 9).

As shown in FIG. 10, the program is begun responsive to the start command 45. Responsive to the sound velocity calculation command 46, the sound velocity of the gas which flows through the flow path 7 is calculated in accordance with eq. (5). Next, responsive to the sound velocity comparison command 47, the various sound velocity values which are previously stored in the sound velocity memory section 12 are compared with the sound velocity value which has been calculated responsive to the sound velocity calculation command 46. Responsive to the gas type identification command 49, the type of gas is identified based on the result of the comparison by the sound velocity comparison command 47.

For example, if the sound velocity c which has been calculated responsive to the sound velocity calculation command 46 satisfies the following formula, then the gas flowing through the flow path 7 is identified as gas B:

$$V2<c<V3.$$

Responsive to the safety standards setting command 50, safety standards corresponding to the identified gas type are set. For example, if the identified gas type is gas B, then continuous use time limits for respective pieces of equipment which use gas B may be set as safety standards.

Responsive to the flow rate compensation coefficient setting command 51, a flow rate compensation coefficient which corresponds to the identified gas type is set. Responsive to the flow rate calculation command 52, a flow rate which corresponds to the identified gas type is calculated in accordance with eq. (4), by using the flow velocity v which has been calculated in accordance with eq. (3) and the flow rate compensation coefficient k which has been set responsive to the flow rate compensation coefficient setting command 51.

Based on the flow rate which has been calculated responsive to the flow rate calculation command 52, the equipment which is being used is inferred. Responsive to the abnormality determination command 53, it is determined whether or not the equipment satisfies the safety standards which have been set responsive to the safety standards setting command 50. For example, it may be determined whether or not the continuous use time which the equipment in question has experienced is within the range of continuous use time limit which has been net responsive to the safety standards setting command 50.

If the equipment does not satisfy the safety standards which have been set responsive to the safety standards netting command 50, then the equipment is determined as being put to "abnormal use" responsive to the abnormality determination command 53, and the valve closing command 55 is executed. As a result, the dual mode valve 32 is closed.

If the equipment satisfies the safety standards which have been set responsive to the safety standards setting command 50, then the equipment is determined as being put to "normal use" responsive to the abnormality determination command 53. After the lapse of an amount of time which is set by an interval setting command 54, the above process is repeated.

Figure 11:
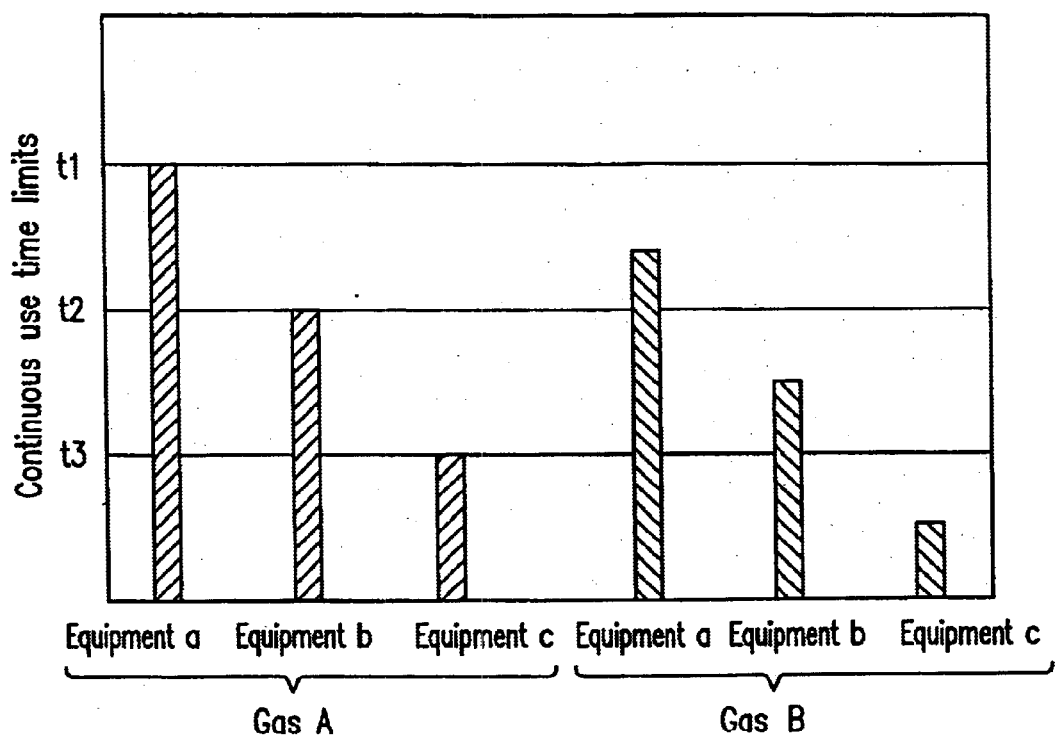
FIG. 11 is a graph showing the relationship between gas equipment and continuous use time limits.

FIG. 11 shows continuous use time limits which are specified for respective places of equipment and gas types, as an exemplification of safety standards such safety standards are specified in order to ensure safe use of gases. In the example shown in FIG. 11, continuous use time limits are specified which correspond to equipment a, b, and c in the case of using gas A, and continuous use time limits are specified which correspond to equipment a, b, and c in the case of using gas B.

As described above, by identifying the gas type based on sound velocity calculation, it is possible to enforce safety standards corresponding to the type of gas which is flowing through the flow path. As a result, safe use of gases can be ensured.

For example, if the gas in use is changed from city gas to propane gas, then the safety standards corresponding to the gas type are automatically changed. Thus, safety is ensured.

The present invention is applicable not only to the case where the gas type changes but also to the case where a component of the gas changes. For example, if the CO density in coal gas is susceptible to changes, safety standards corresponding to its density can be set, thereby ensuring safety in accordance with the changes in the CO density.

Although some applications for fuel gases have been illustrated as examples of the present invention, the gases for which the present invention is suitable are not limited thereto. Hospitals may use various gases for medical purposes. The above three examples are also applicable to such gases. For example, an application is contemplated where the supply of any wrong gas may be immediately shut by distinguishing oxygen from nitrogen. The above three examples are also applicable to various gases which are used in the field of semiconductor production.

EXAMPLE 4

Figure 12:
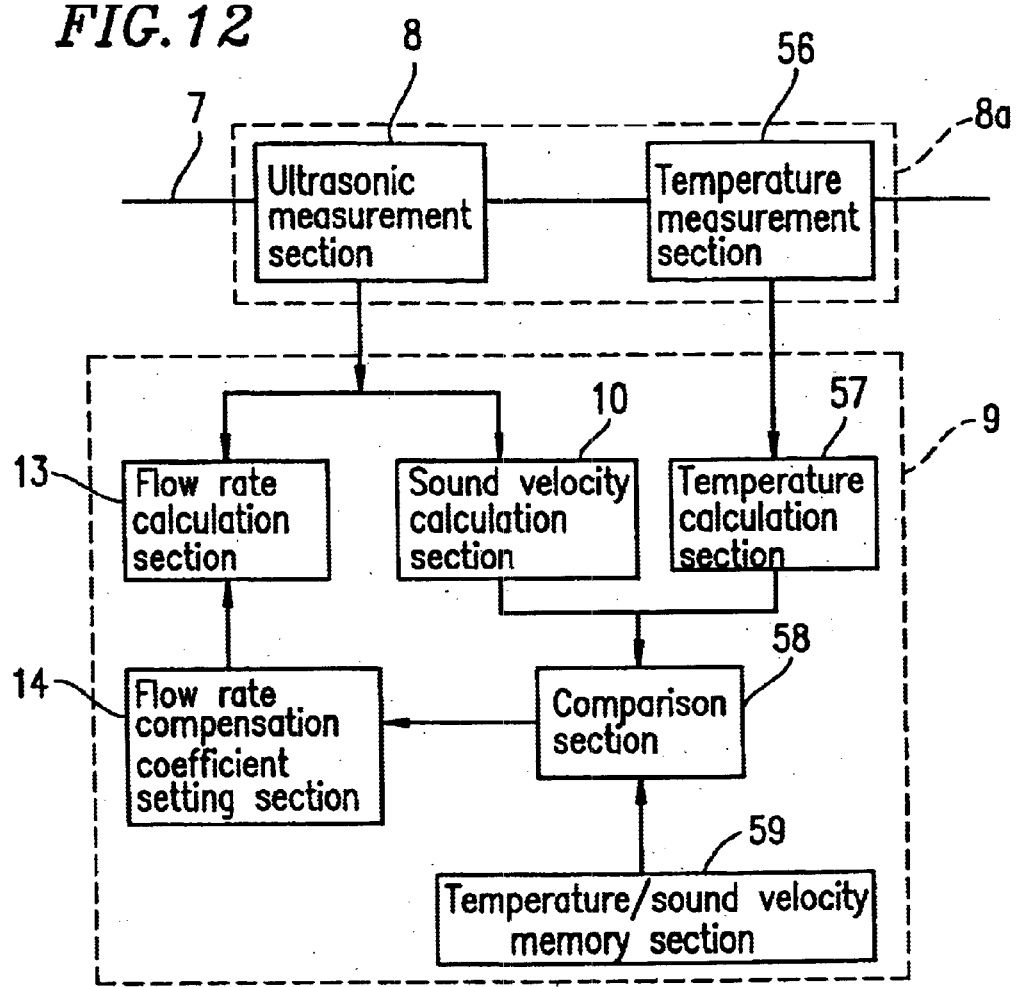
FIG. 12 is a block diagram showing the structure of a gas type identification system according to Example 4 of the present invention.

FIG. 12 shows the structure of a gas type identification system according to Example 4 of the present invention.

As shown in FIG. 12, the gas type identification system includes a flow path 7, an ultrasonic measurement section 8 disposed in the flow path 7, a temperature measurement section 56 disposed in the flow path 7, and a calculation section 9 for calculating a signal which is output from the ultrasonic measurement section 8 and a signal which is output from the temperature measurement section 56.

In Example 4, the same constituent elements as those in Example 1 are indicated by like reference numerals, and the descriptions thereof are omitted.

In FIG. 12, reference numeral 8a denotes a measurement section. The measurement section 8a includes the ultrasonic measurement section 8 and the temperature measurement section 56. Reference numeral 57 denotes a temperature calculation section; 58 denotes a comparison section; and 59 denotes a temperature/sound velocity memory section.

Figure 13:
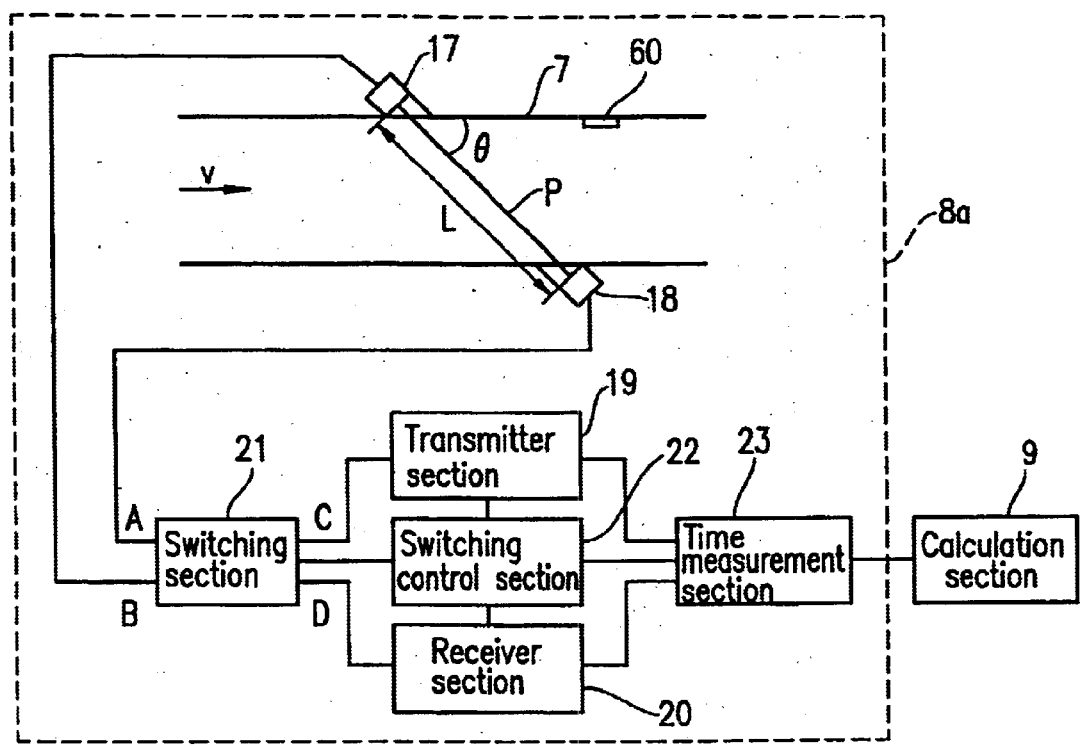
FIG. 13 is a block diagram showing the structure of a measurement section in a gas type identification system.

FIG. 13 shows the structure of the measurement section 8a shown in FIG. 12.

In FIG. 13, reference numeral 60 denotes a temperature sensor which functions as the temperature measurement section. The temperature sensor 60 is disposed in the vicinity of an ultrasonic transducer 17 or 18 in the interior of the flow path 7.

Next, the operation and functions of the gas type identification system will be described.

Referring to FIG. 12, the calculation section 9 performs calculation based on a signal which is output from the ultrasonic measurement section 8 and a signal which is output from the temperature measurement section 56. The sound velocity calculation section 10 calculates the sound velocity of the gas flowing through the flow path 7, and the temperature calculation section 57 calculates the temperature of the gas flowing through the flow path 7. The comparison section 58 compares the sound velocity value which has been calculated by the sound velocity calculation section 10 with a sound velocity value(s) which is previously stored in the temperature/sound velocity memory section 59, and compares the temperature value which has been calculated by the temperature calculation section 57 with a temperature value(s) which is previously stored in the temperature/sound velocity memory section 59. The type of gas is identified based on the result of the comparison by the comparison section 58. A flow rate compensation coefficient which corresponds to the identified gas type is set by the flow rate compensation coefficient setting section 14. The flow rate calculation section 13 calculates a flow rate based on a signal which is output from the ultrasonic measurement section 8 by using the flow rate compensation coefficient which has been set by the flow rate compensation coefficient setting section 14.

Since the method of flow rate measurement is similar to that in Example 1, the description thereof is omitted herein.

Figure 14:
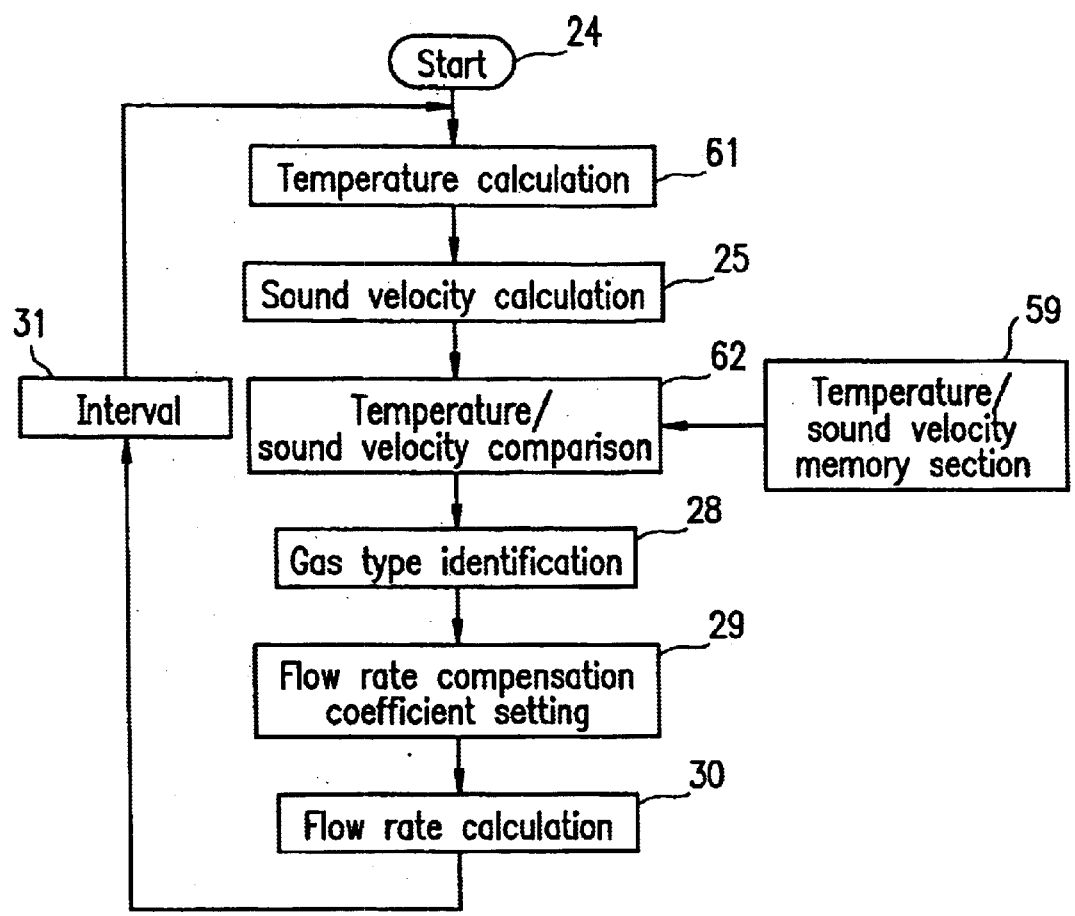
FIG. 14 is a flowchart showing the procedure to be performed by a calculation section in a gas type identification system.

FIG. 14 shows the procedure to be performed by the calculation section 9 shown in FIG. 12.

In FIG. 14, reference numeral 61 denotes a temperature calculation command; and 62 denotes a temperature/sound velocity comparison command.

The temperature calculation command 61 corresponds to the temperature calculation section 57. The temperature/sound velocity comparison command 62 corresponds to comparison section 58.

As shown in FIG. 14, the program is begun responsive to the start command 24. Responsive to the temperature calculation command 61, the temperature of the gas which flows through the flow path 7 is calculated. Responsive to the sound velocity calculation command 25, the sound velocity of the gas which flows through the flow path 7 is calculated in accordance with eq. (5). Next, responsive to the temperature/sound velocity comparison command 62, the various temperature values which are previously stored in the temperature/sound velocity memory section 59 are compared with the temperature value which has been calculated responsive to the temperature calculation command 61, and the various sound velocity values which are previously stored in the temperature/sound velocity memory section 59 are compared with the sound velocity which has been calculated responsive to the sound velocity calculation command 25. Responsive to the gas type identification command 28, the type of gas is identified based on the result of the comparison by the temperature/sound velocity comparison command 62.

Responsive to the flow rate compensation coefficient setting command 29, a flow rate compensation coefficient which corresponds to the identified gas type is set. Responsive to the flow rate calculation command 30, a flow rate which corresponds to the identified gas type is calculated in accordance with eq. (4), by using the flow velocity v which has been calculated in accordance with eq. (3) and the flow rate compensation coefficient k which has been set responsive to the flow rate compensation coefficient setting command 29.

The above process is repeated after the lapse of an amount of time which is set by an interval setting command 31. In this process, if the gas type is changed, a flow rate corresponding to the gas type after the change will be calculated.

Figure 15:
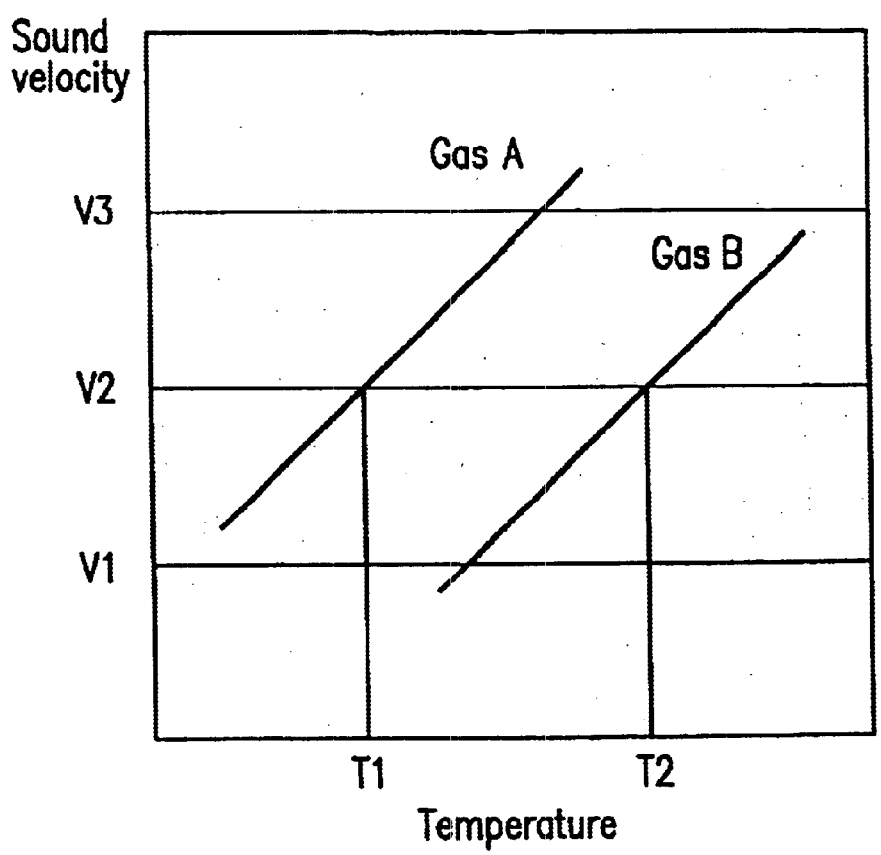
FIG. 15 is a graph showing the relationship between gas types, temperatures, and sound velocities.

FIG. 15 shows the relationship between gas types, temperatures, and sound velocities. Some gases may be unidentified based on sound velocity alone but may become identifiable based on the combinations of temperature and sound velocity. For example, gas A and gas B shown in FIG. 15 can be clearly distinguished by calculating their temperatures and sound velocities. The relationship between gas types, temperatures, and sound velocities such as that shown in FIG. 15 can be retained in the form of some formulae or a table. In the present example, such relationship is stored in the temperature/sound velocity memory section 59.

For example, if the temperature T which has been calculated responsive to the temperature calculation command 61 and the sound velocity c which has been calculated responsive to the sound velocity calculation command 25 satisfy the following formulae, then the gas flowing through the flow path 7 is identified as gas A:

$T=T1$ $c=V2$

As described above, by using temperature and sound velocity, it is possible to identify gas types even among gases which have relatively close sound velocity values.

EXAMPLE 5

Figure 16:
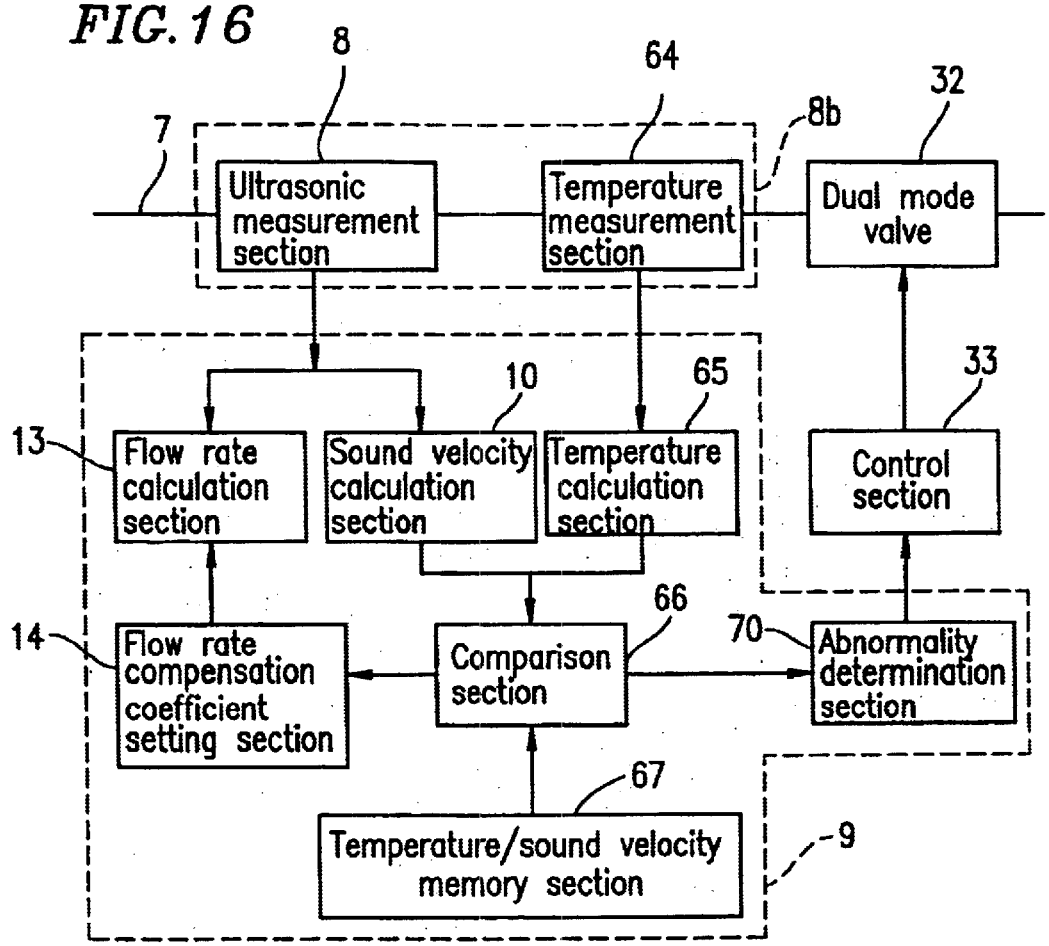
FIG. 16 is a block diagram showing the structure of a gas type identification system according to Example 5 of the present invention.

FIG. 16 shows the structure of a gas type identification system according to Example 5 of the present invention.

As shown in FIG. 16, the gas type identification system includes a flow path 7, an ultrasonic measurement section 8 disposed in the flow path 7, a temperature measurement section 64 disposed in the flow path 7, a calculation section 9 for performing a mathematical operation for a signal which is output from the ultrasonic measurement section 8 and a signal which is output from the temperature measurement section 64, a dual mode valve 32 disposed in the flow path 7, and a control section 33 for controlling the dual mode valve 32. The dual mode valve 32 is disposed downstream from the ultrasonic measurement section 8 in the flow path 7.

In Example 5, the same constituent elements as those in Example 2 are indicated by like reference numerals, and the descriptions thereof are omitted.

In FIG. 16, reference numeral 8b denotes a measurement section. The measurement section 8b includes the ultrasonic measurement section 8 and the temperature measurement section 64. Reference numeral 65 denotes a temperature calculation section; 66 denotes a comparison section; 67 denotes a temperature/sound velocity memory section; and 70 denotes an abnormality determination section.

The structure of the measurement section 8b is the same as that of the measurement section 8a shown in FIG. 13.

Figure 17:
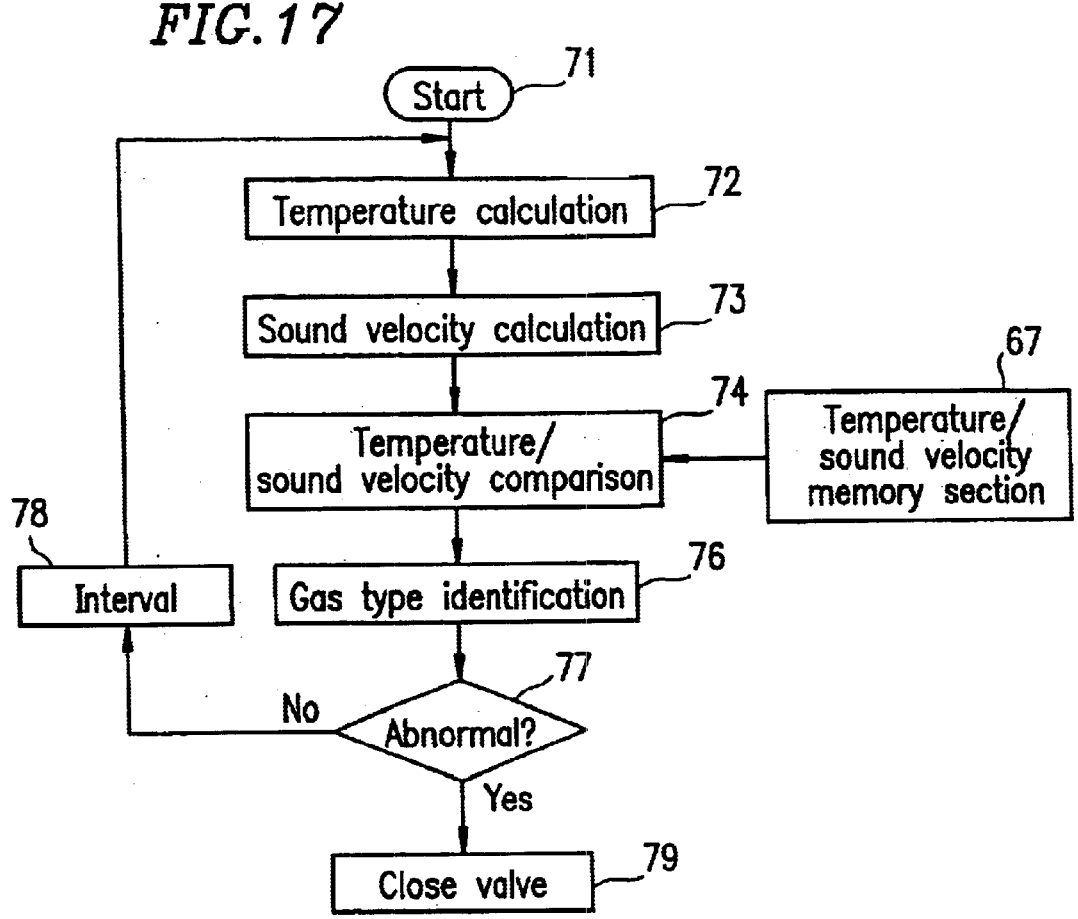
FIG. 17 is a flowchart showing the procedure to be performed by a calculation section in a gas type identification system.

FIG. 17 shows the procedure to be performed by the calculation section 9 shown in FIG. 16.

Now, it is assumed that gas B is actually flowing through the flow path 7 instead of gas A, which is expected to be flowing through the flow path 7.

As shown in FIG. 17, the program is begun responsive to the start command 71. Responsive to the temperature calculation command 72, the temperature of the gas which flows through the flow path 7 is calculated. Responsive to the sound velocity calculation command 73, the sound velocity of the gas which flows through the flow path 7 is calculated in accordance with eq. (5). Next, responsive to the temperature/sound velocity comparison command 74, the various temperature values which are previously stored in the temperature/sound velocity memory section 67 are compared with the temperature value which has been calculated responsive to the temperature calculation command 72, and the various sound velocity values which are previously stored in the temperature/sound velocity memory section 67 are compared with the sound velocity which has been calculated responsive to the sound velocity calculation command 73. Responsive to the gas type identification command 76, the type of gas is identified based on the result of the comparison by the temperature/sound velocity comparison command 74.

For example, if the temperature T which has been calculated responsive to the temperature calculation command 72 and the sound velocity c which has been calculated responsive to the sound velocity calculation command 73 satisfy the following formulae, then the gas flowing through the flow path 7 is identified as gas B in FIG. 15:

$$T=T2$$

$$c=V2$$

In this case, since gas B has flowed through the flow path 7 instead of gas A, it is determined that "an abnormal gas is flowing through the flow path 7" responsive to the abnormality determination command 77, and the valve closing command 79 is executed. As a result, the dual mode valve 32 is closed.

If the gas flowing through the flow path 7 is identified as gas A, it is determined that "a normal gas tis flowing through the flow path 7" responsive to the abnormality determination command 77. After the lapse of an amount of time which is set by an interval setting command 78, the above process is repeated.

As described above, by using temperature and sound velocity, it is possible to identify gas types even among gases which have relatively close sound velocity values, and to immediately shut off the flow of any gas that is not the specified gas, thereby providing for safety

EXAMPLE 6

Figure 18:
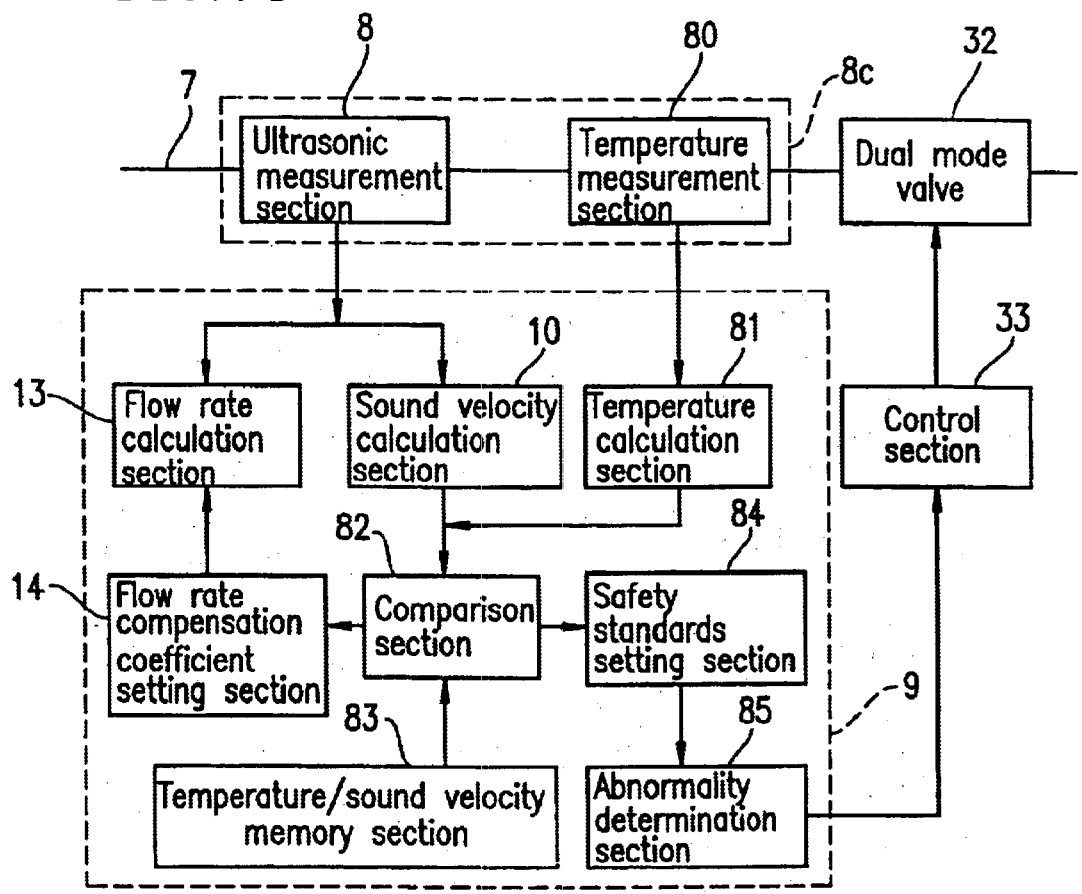
FIG. 18 is a block diagram showing the structure of a gas type identification system according to Example 6 of the present invention.

FIG. 18 shows the structure of a gas type identification system according to Example 6 of the present invention.

As shown in FIG. 18, the gas type identification system includes a flow path 7, an ultrasonic measurement section 8 disposed in the flow path 7, a temperature measurement section 80 disposed in the flow path 7, a calculation section 9 for performing a mathematical operation for a signal which is output from the ultrasonic measurement section 8 and a signal which is output from the temperature measurement section 80, a dual mode valve 32 disposed in the flow path 7, and a control section 33 for controlling the dual mode valve 32. The dual mode valve 32 is disposed downstream from the ultrasonic measurement section 8 in the flow path 7.

In Example 6, the same constituent elements as those in Example 3 are indicated by like reference numerals, and the descriptions thereof are omitted.

In FIG. 18, reference numeral 8c denotes a measurement section. The measurement section 8c includes the ultrasonic measurement section 8 and the temperature measurement section 80. Reference numeral 81 denotes a temperature calculation section; 82 denotes a comparison section; 83 denotes a temperature/sound velocity memory section; 84 denotes a safety standards setting section; and 85 denotes an abnormality determination section.

The structure of the measurement section 8c is the same as that of the measurement section 8a shown in FIG. 13.

Figure 19:
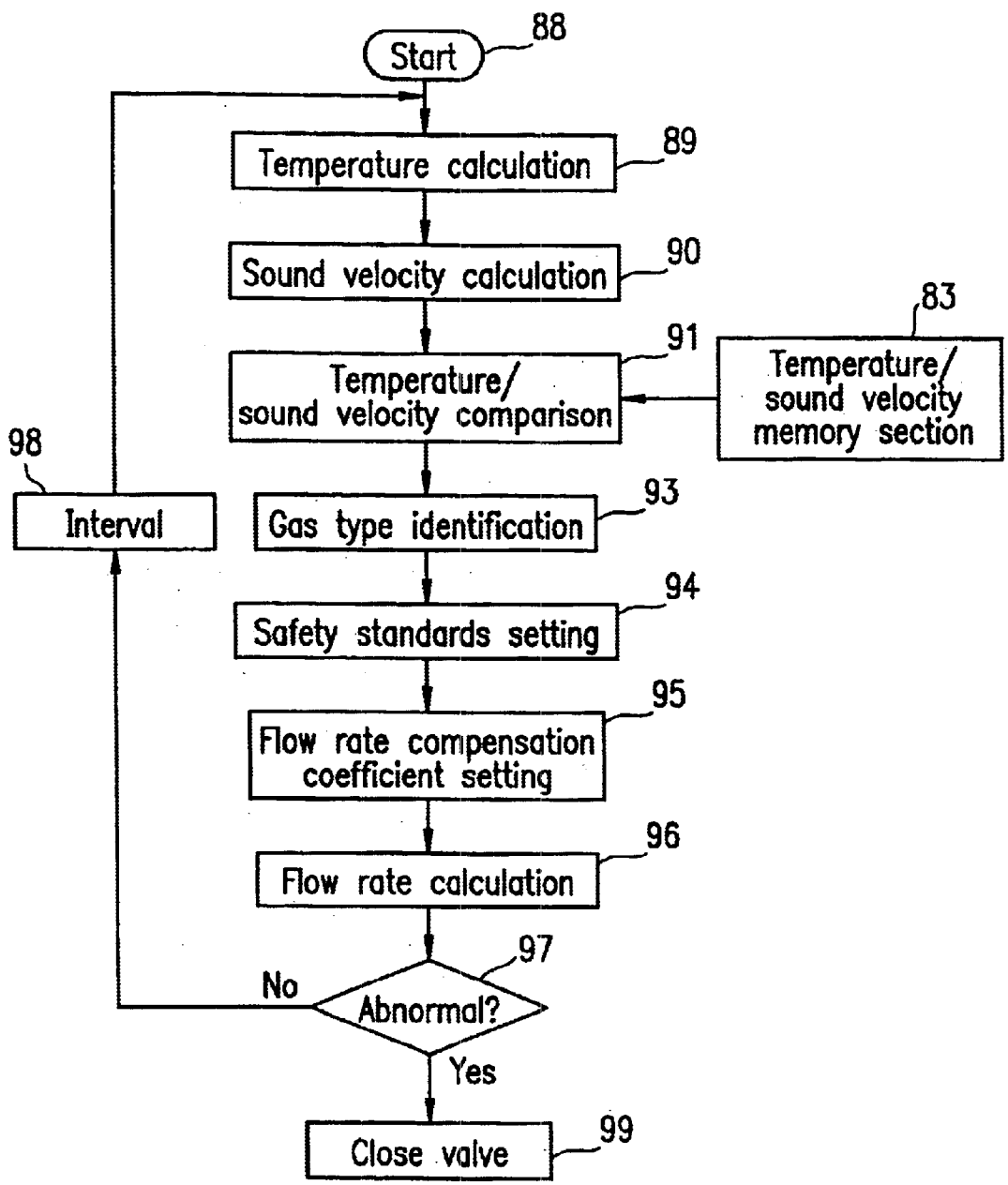
FIG. 19 is a flowchart showing the procedure to be performed by a calculation section in a gas type identification system.

FIG. 19 shows the procedure to be performed by the calculation section 9 shown in FIG. 18.

As shown in FIG. 19, the program is begun responsive to the start command 88. Responsive to the temperature calculation command 89, the temperature of the gas which flows through the flow path 7 is calculated. Responsive to the sound velocity calculation command 90, the sound velocity of the gas which flows through the flow path 7 is calculated in accordance with eq. (5). Next, responsive to the temperature/sound velocity comparison command 91, the various temperature values which are previously stored in the temperature/sound velocity memory section 83 are compared with the temperature value which has been calculated responsive to the temperature calculation command 89, and the various sound velocity values which are previously stored in the temperature/sound velocity memory section 83 are compared with the sound velocity which has been calculated responsive to the sound velocity calculation command 90. Responsive to the gas type identification command 93, the type of gas is identified based on the result of the comparison by the temperature/sound velocity comparison command 91.

For example, if the temperature T which has been calculated responsive to the temperature calculation command 89 and the sound velocity c which has been calculated responsive to the sound velocity calculation command 90 satisfy the following formulae, then the gas flowing through the flow path 7 is identified as gas B in FIG. 15:

$$T=T2$$

$$c=V2$$

Responsive to the safety standards setting command 94, safety standards corresponding to the identified gas type are set. For example, if the identified gas type is gas B, then continuous use time limits for respective pieces of equipment which use gas B may be set as safety standards.

Responsive to the flow rate compensation coefficient setting command 95, a flow rate compensation coefficient which corresponds to the identified gas type is set. Responsive to the flow rate calculation command 96, a flow rate which corresponds to the identified gas type is calculated in accordance with eq. (4), by using the flow velocity v which has been calculated in accordance with eq. (3) and the flow rate compensation coefficient k which has been set responsive to the flow rate compensation coefficient setting command 95.

Based on the flow rate which has been calculated responsive to the flow rate calculation command 96, the equipment which is being used is inferred. Responsive to the abnormality determination command 97, it is determined whether or not the equipment satisfies the safety standards which have been set responsive to the safety standards setting command 94. For example, it may be determined whether or not the continuous use time which the equipment in question has experienced is within the range of continuous use time limit which has been set responsive to the safety standards setting command 94.

If the equipment does not satisfy the safety standards which have been set responsive to the safety standards setting command 94, then the equipment is determined as being put to "abnormal use" responsive to the abnormality determination command 97, and the valve closing command 99 is executed. As a result, the dual mode valve 32 is closed.

If the equipment satisfies the safety standards which have been set responsive to the safety standards setting command 94, then the equipment is determined as being put to "normal use" responsive to the abnormality determination command 97. After the lapse of an amount of time which is set by an interval setting command 98, the above process is repeated.

As described above, by using temperature and sound velocity, it is possible to identify gas types even among gases which have relatively close sound velocity values, and to enforce safety standards corresponding to the type of gas which is flowing through the flow path. As a result, safe use of gases can be ensured.

EXAMPLE 7

Hereinafter, a gas type identification system according to Example 7 of the present invention will be described. The structure of the gas type identification system according to Example 7 of the present invention is the same as that of the gas type identification system according to Example 4 of the present invention. Therefore, the description thereof is omitted herein.

Figure 20:
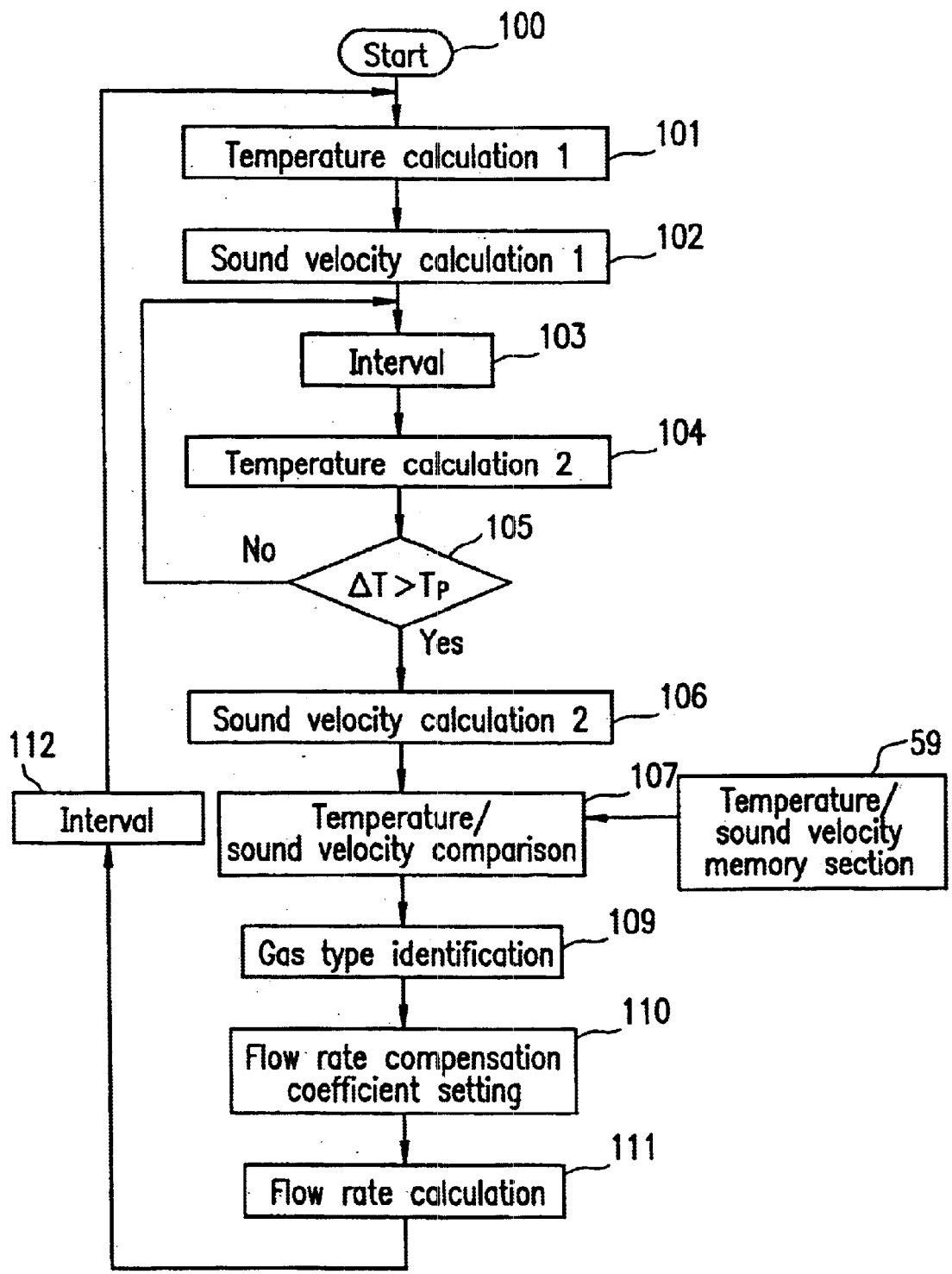
FIG. 20 is a flowchart showing the procedure to be performed by a calculation section in a gas type identification system according to Example 7 of the present invention.

FIG. 20 shows the procedure to be performed by a calculation section in the gas type identification system according to Example 7 of the present invention.

As shown in FIG. 20, the program is begun responsive to the start command 100. Responsive to a 1st temperature calculation command 101, the temperature T1 of the gas which flows through the flow path 7 is calculated. Responsive to a 1st sound velocity calculation command 102, the sound velocity of the gas which flows through the flow path 7 is calculated. Responsive to a 2nd temperature calculation command 104, the temperature T2 of the gas which flows through the flow path 7 is calculated.

Responsive to a comparison command 105, it is determined whether a difference ΔT between the temperature T1 and the temperature T2 is greater than a predetermined temperature Tp or not. If the difference ΔT is equal to or smaller than the predetermined temperature Tp, the process is continued after the lapse of an amount of time which is set by an interval setting command 103. If the difference ΔT is greater than the predetermined temperature Tp, the sound velocity of the gas flowing through the flow path 7 is calculated responsive to a 2nd sound velocity calculation command 106.

Thus, two pairs of temperature values and sound velocity values are calculated.

Responsive to a temperature/sound velocity comparison command 107, the various temperature values which are previously stored in the temperature/sound velocity memory section 59 are compared with the two calculated temperature values, and the various sound velocity values which are previously stored in the temperature/sound velocity memory section 59 are compared with the two calculated sound velocity values. Responsive to a gas type identification command 109, the type of gas is identified based on the results of comparison by the temperature/sound velocity comparison command 107.

Responsive to a flow rate compensation coefficient setting command 110, a flow rate compensation coefficient which corresponds to the identified gas type is set. Responsive to the flow rate calculation command 111, a flow rate which corresponds to the identified gas type is calculated in accordance with eq. (4), by using the flow velocity v which has been calculated in accordance with eq. (3) and the flow rate compensation coefficient k which has been set responsive to the flow rate compensation coefficient setting command 110.

The above process is repeated after the lapse of an amount of time which is set by an interval setting command 112. In this process, if the gas type is changed, a flow rate corresponding to the gas type after the change will be calculated.

Figure 21:
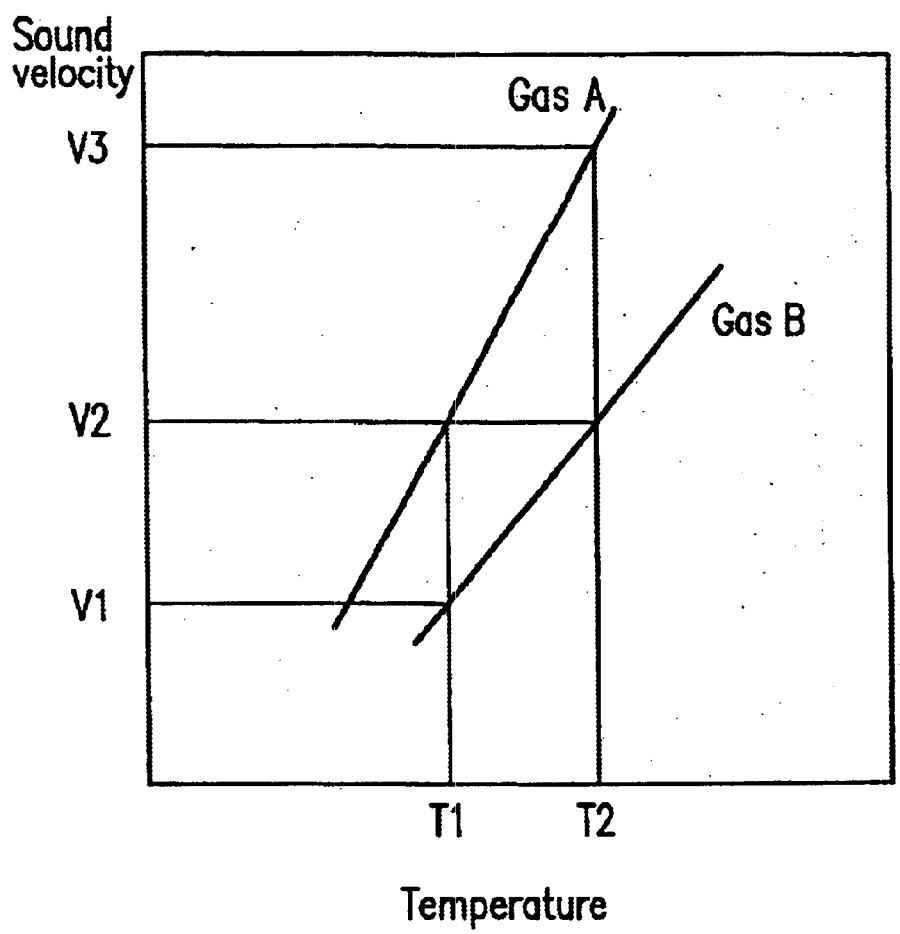
FIG. 21 is a graph showing the relationship between gas types, temperatures, and sound velocities.

FIG. 21 shows the relationship between gas types, temperatures, and sound velocities. Gas A and gas B can be clearly distinguished by calculating their sound velocity values at temperature T1 and their sound velocity values at temperature T2. The relationship between gas types, temperatures, and sound velocities such as that shown in FIG. 21 can be retained in the form of some formulae or a table. In the present example, such relationship is stored in the temperature/sound velocity memory section 59.

As described above, by using two pairs of temperature values and sound velocity values, it is possible to identify gas types even among gases which have relatively close sound velocity values.

EXAMPLE 8

Hereinafter, a gas type identification system according to Example 8 of the present invention will be described. The structure of the gas type identification system according to Example 8 of the present invention is the same as that of the gas type identification system according to Example 5 of the present invention. Therefore, the description thereof is omitted herein.

The gas type identification system according to Example 8 of the present invention identifies gas types by using two pairs of temperature values and sound velocity values as described in Example 7, and determines whether or not an abnormal gas is flowing through the flow path 7.

Figure 22:
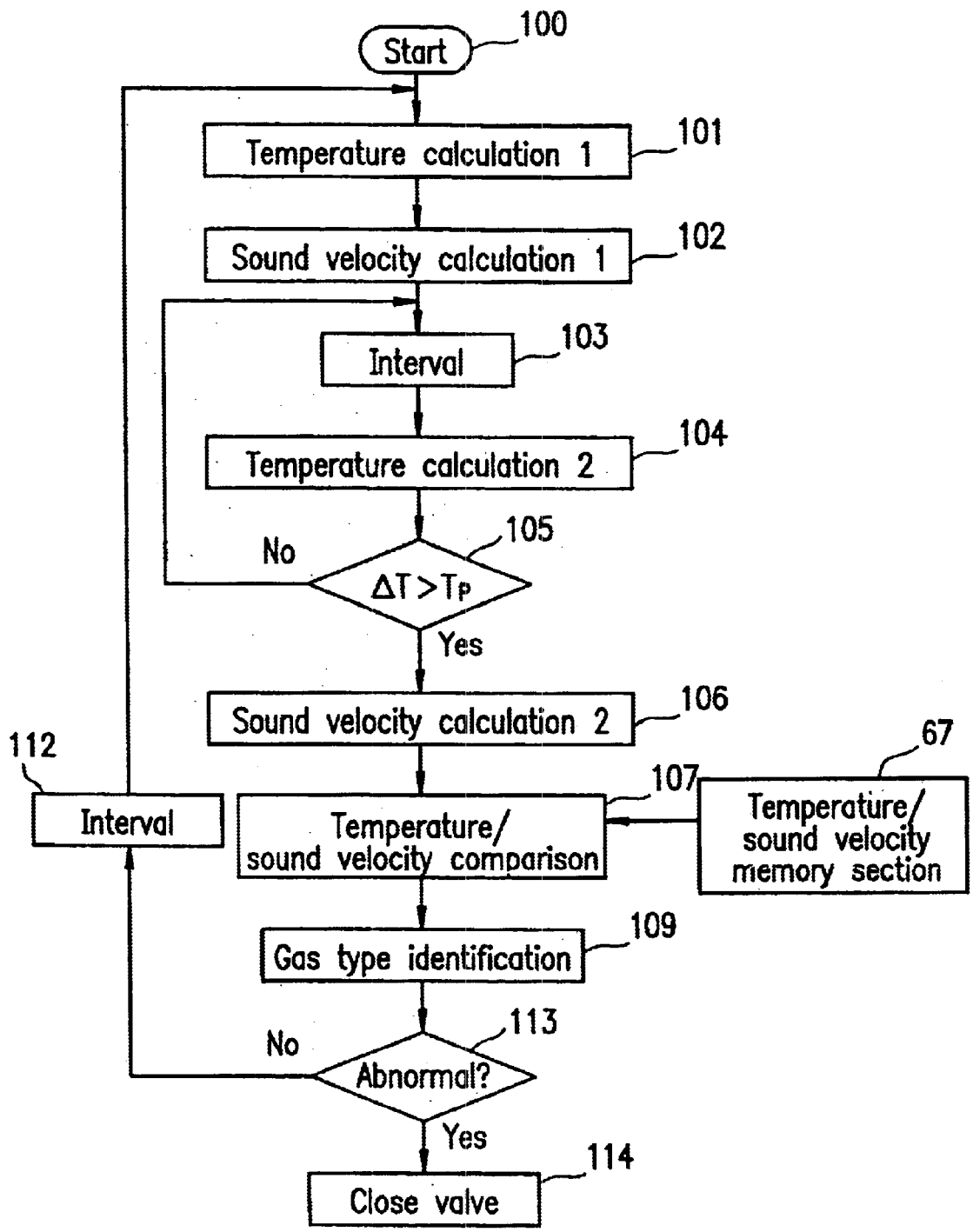
FIG. 22 is a flowchart showing the procedure to be performed by a calculation section in a gas type identification system according to Example 8 of the present invention.

FIG. 22 shows the procedure to be performed by a calculation section in the gas type identification system according to Example 8 of the present invention.

As shown in FIG. 22, the procedure from a start command 100 to a gas type identification command 109 is the same as that of the flow shown in FIG. 20. Therefore, the description thereof is omitted herein.

Now, it is assumed that gas B is actually flowing through the flow path 7 instead of gas A, which is expected to be flowing through the flow path 7, and further that the gas flowing through the flow path 7 has been determined as gas B responsive to the gas type identification command 109.

In this case, it is determined that "an abnormal gas is flowing through the flow path 7" responsive to an abnormality determination command 113, and a valve closing command 114 is executed. As a result, the dual mode valve 32 is closed.

If the gas flowing through the flow path 7 is identified as gas A, it is determined that "a normal gas is flowing through the flow path 7" responsive to the abnormality determination command 113. After the lapse of an amount of time which is set by an interval setting command 112, the above process is repeated.

As described above, by using two pairs of temperature values and sound velocity values, it is possible to identify gas types even among gases which have relatively close sound velocity values, and to immediately shut off the flow of any gas that is not the specified gas, thereby providing for safety.

EXAMPLE 9

Hereinafter, a gas type identification system according to Example 9 of the present invention will be described. The structure of the gas type identification system according to Example 9 of the present invention is the same as that of the gas type identification system according to Example 6 of the present invention. Therefore, the description thereof is omitted herein.

The gas type identification system according to Example 9 of the present invention identifies gas types by using two pairs of temperature values and sound velocity values as described in Example 7, and determines whether or not the safety standards corresponding to the identified gas type are satisfied.

Figure 23:
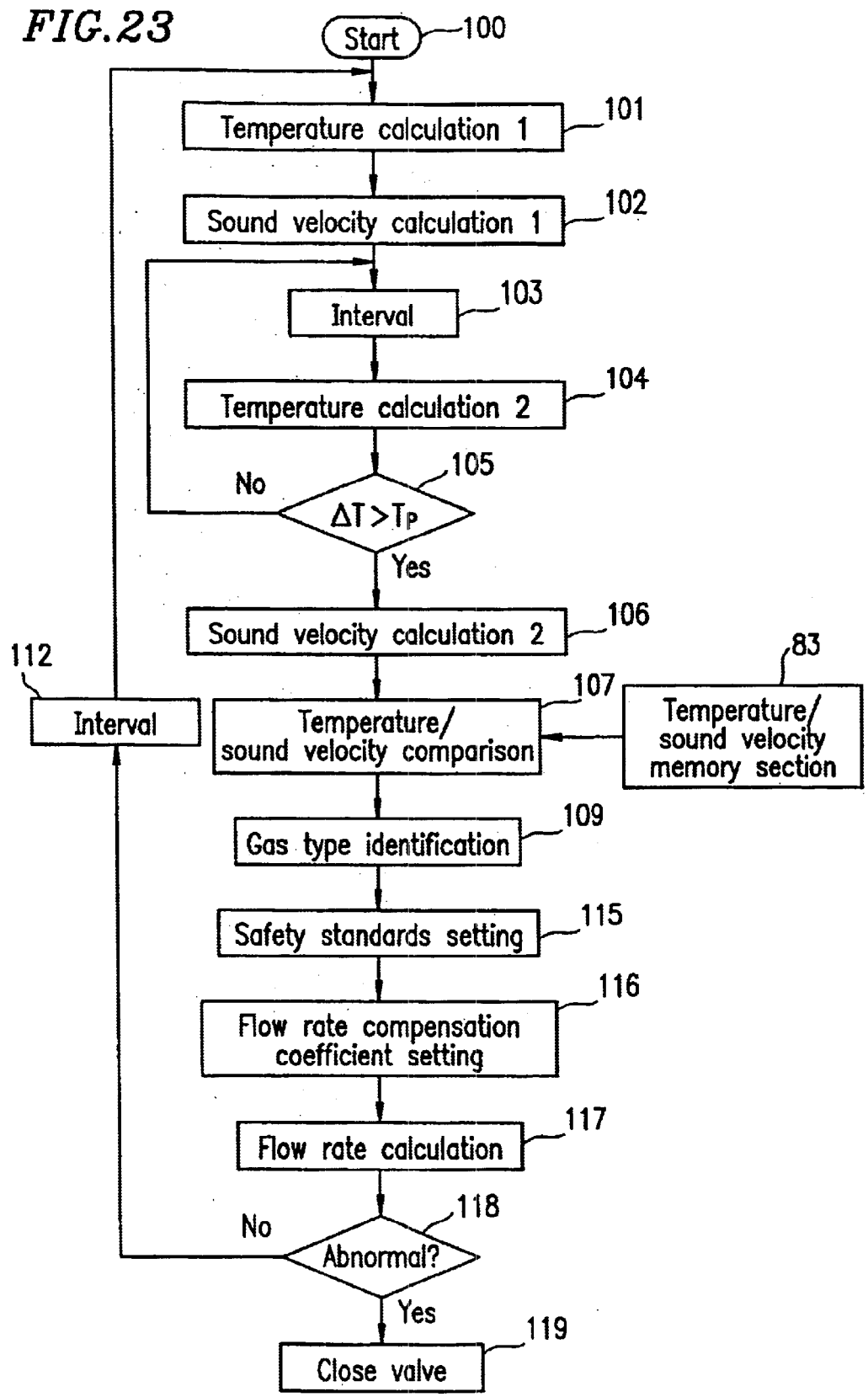
FIG. 23 is a flowchart showing the procedure to be performed by a calculation section in a gas type identification system according to Example 9 of the present invention.

FIG. 23 shows the procedure to be performed by a calculation section in the gas type identification system according to Example 9 of the present invention.

As shown in FIG. 23, the procedure from a start command 100 to a gas type identification command 109 is the same as that of the flow shown in FIG. 20. Therefore, the description thereof is omitted herein.

The process after a safety standards setting command 115 is the same as that described in Example 6.

As described above, by using two pairs of temperature values and sound velocity values, it is possible to identify gas types even among gases which have relatively close sound velocity values, and to enforce safety standards corresponding to the type of gas which is flowing through the flow path. As a result, safe use of gases can be ensured.

In all of the above examples, it is possible to additionally perform temperature compensation for gas flow rates where the gas type and the temperature are known. In particular, in the case where the repertoire of gas types is known in advance so that it is unnecessary to know the temperature to identify gas types as in Example 1, it is possible to infer temperature from sound velocity; therefore, it is possible to perform temperature compensation without employing a temperature sensor.

By additionally employing a pressure sensor, it also becomes possible to perform mass flow rate measurement.

INDUSTRIAL APPLICABILITY

In accordance with a gas type identification system of the present invention, the type of gas flowing through the flow path is automatically identified, and a flow rate compensation coefficient which corresponds to the identified gas type is set. Accordingly, there is provided an advantage in that a system or equipment can be constructed which supports various gas types.

In accordance with another gas type identification system of the present invention, a gas type is automatically identified, and a dual mode valve which is disposed in a flow path is controlled in accordance with the identified gas type. Accordingly, there is provided an advantage in that it is possible to prevent unsafe situations in the use of a system or equipment where the type of gas flowing through the flow path changes.

In accordance with another gas type identification system of the present invention, a gas type is automatically identified, and safety standards corresponding to the identified gas type are set. Accordingly, there is provided an advantage in that it is possible to prevent unsafe situations in the use of a system or equipment where the type of gas flowing through the flow path changes.

In accordance with another gas type identification system of the present invention, a gas type is automatically identified by using a temperature value and a sound velocity value. Accordingly, there is provided an advantage in that it is possible to identify gas types even among gases which have relatively close sound velocity values.

In accordance with another gas type identification system of the present invention, a gas type is automatically identified by using a temperature value and a sound velocity value. Accordingly, there is provided an advantage in that it is possible to identify gas types even among gases which have relatively close sound velocity values and in that it is possible to immediately shut off the flow of any gas that is not the specified gas, thereby ensuring safe use of gases.

In accordance with another gas type identification system of the present invention, a gas type is automatically identified by using a temperature value and a sound velocity value. Accordingly, there is provided an advantage in that it is possible to identify gas types even among gases which have relatively close sound velocity values and in that it is possible to enforce safety standards corresponding to the type of gas which is flowing through the flow path, thereby ensuring safe use of gases.

In accordance with another gas type identification system of the present invention, a gas type is automatically identified by using two pairs of temperature values and sound velocity values. Accordingly, there is provided an advantage in that it is possible to identify gas types even among gases which have relatively close sound velocity values.

In accordance with another gas type identification system of the present invention, a gas type is automatically identified by using two pairs of temperature values and sound velocity values. Accordingly, there is provided an advantage in that it is possible to identify gas types even among gases which have relatively close sound velocity values and in that it is possible to immediately shut off the flow of any gas that is not the specified gas, thereby ensuring safe use of gases.

In accordance with another gas type identification system of the present invention, a gas type is automatically identified by using two pairs of temperature values and a velocity values. Accordingly, there is provided an advantage in that it is possible to identify gas types even among gases which have relatively close sound velocity values and in that it is possible to enforce safety standards corresponding to the type of gas which is flowing through the flow path, thereby ensuring safe use of gases.

What is claimed is:

1. A gas type identification system comprising:
   a flow path;

an ultrasonic measurement section disposed in the flow path, the ultrasonic measurement section including a pair of ultrasonic transducers;

a flow rate calculation section for calculating a flow rate of a gas flowing through the flow path based on a signal from the ultrasonic measurement section;

a sound velocity calculation section for calculating a sound velocity of a gas flowing through the flow path based on a signal from the ultrasonic measurement section;

a sound velocity memory section for previously storing a relationship between gas types and predetermined sound velocities; and a comparison section for comparing the sound velocity calculated by the sound velocity calculation section with at least one of the predetermined sound velocities in the relationship previously stored in the sound velocity memory section and for identifying a gas type of the gas flowing through the flow path in accordance with a result of the comparison.

2. A gas type identification system according to claim 1, wherein the gas type identification system further comprises:

a dual mode valve disposed in the flow path;

a safety standards setting section for setting safety standards in accordance with a the result of the comparison by the comparison section;

a determination section for determining whether or not the safety standards are satisfied; and a control section for controlling the dual mode valve in accordance with a result of the determination by the determination section.

3. A gas type identification system comprising:

a flow path;

an ultrasonic measurement section disposed in the flow path, the ultrasonic measurement section including a pair of ultrasonic transducers;

a flow rate calculation section for calculating a flow rate of a gas flowing through the flow path based on a signal from the ultrasonic measurement section;

a sound velocity calculation section for calculating a sound velocity of a gas flowing through the flow path based on a signal from the ultrasonic measurement section;

a sound velocity memory section for previously storing a relationship between gas types and predetermined sound velocities;

a comparison section for comparing the sound velocity calculated by the sound velocity calculation section with at least one of the predetermined sound velocities in the relationship previously stored in the sound velocity memory section and for identifying a gas type of the gas flowing through the flow path in accordance with a result of the comparison;

a flow rate compensation coefficient setting section for setting a flow rate compensation coefficient dependant on the gas type identified by the comparison section; and a flow rate calculation section for calculating a flow rate of the gas flowing through the flow path based on the signal from the ultrasonic measurement section and the flow rate compensation coefficient.

4. A gas type identification system comprising:

a flow path;

an ultrasonic measurement section disposed in the flow path, the ultrasonic measurement section including a pair of ultrasonic transducers;

a flow rate calculation section for calculating a flow rate of a gas flowing through the flow path based on a signal from the ultrasonic measurement section;

a sound velocity calculation section for calculating a sound velocity of a gas flowing through the flow path based on a signal from the ultrasonic measurement section;

a sound velocity memory section for previously storing a relationship between gas types and predetermined sound velocities;

a comparison section for comparing the sound velocity calculated by the sound velocity calculation section with at least one of the predetermined sound velocities in the relationship previously stored in the sound velocity memory section and for identifying a gas type of the gas flowing through the flow path in accordance with a result of the comparison;

a dual mode valve disposed upstream from the ultrasonic measurement section in the flow path; and a control section for controlling the dual mode valve in accordance with the result of the comparison by the comparison section.

5. A gas type identification system comprising:

a flow path;

a temperature measurement section disposed in the flow path;

a temperature calculation section for calculating a temperature of a gas flowing through the flow path based on the temperature measurement section;

an ultrasonic measurement section disposed in the flow path, the ultrasonic measurement section including a pair of ultrasonic transducers;

a flow rate calculation section for calculating a flow rate of a gas flowing through the flow path based on signals resulting from a plurality of measurements performed by the ultrasonic measurement section;

a sound velocity calculation section for calculating a sound velocity of the gas flowing through the flow path based on a signal from the ultrasonic measurement section;

a temperature/sound velocity memory section for previously storing a relationship between gas types, predetermined temperatures and predetermined sound velocities; and a comparison section for comparing the temperature calculated by the temperature calculation section with at least one of the predetermined temperatures in the relationship previously stored in the temperature/sound velocity memory section, for comparing the sound velocity calculated by the sound velocity calculation section with at least one of the predetermined sound velocities in the relationship previously stored in the temperature/sound velocity memory section and for identifying a gas type of the gas flowing through the flow path in accordance with a result of the comparison.

6. A gas type identification system according to claim 5, wherein the gas type identification system further comprises:

a dual mode valve disposed in the flow path;

a safety standards setting section for setting safety standards in accordance with the result of the comparison by the comparison section;

a determination section for determining whether or not the safety standards are satisfied; and a control section for controlling the dual mode valve in accordance with a result of the determination by the determination section.

7. A gas type identification system comprising:

a flow path;

a temperature measurement section disposed in the flow path;

a temperature calculation section for calculating a temperature of a gas flowing through the flow path based on a signal from the temperature measurement section;

an ultrasonic measurement section disposed in the flow path, the ultrasonic measurement section including a pair of ultrasonic transducers;

a flow rate calculation section for calculating a flow rate of a gas flowing through the flow path based on a signal from the ultrasonic measurement section;

a sound velocity calculation section for calculating a sound velocity of the gas flowing through the flow path based on a signal from the ultrasonic measurement section;

a temperature/sound velocity memory section for previously storing a relationship between gas types, predetermined temperatures and predetermined sound velocities;

a comparison section for comparing the temperature calculated by the temperature calculation section with at least one of the predetermined temperatures in the relationship previously stored in the temperature/sound velocity memory section for comparing the sound velocity calculated by the sound velocity calculation section, with at least one of the predetermined sound velocities in the relationship previously stored in the temperature/sound velocity memory section and for identifying a gas type of the gas flowing through the flow path in accordance with a result of the comparison;

a flow rate compensation coefficient setting section for setting a flow rate compensation coefficient dependent on the gas type identified by the comparison section; and a flow rate calculation section for calculating a flow rate of the gas flowing through the flow path based on the signal from the ultrasonic measurement section and the flow rate compensation coefficient.

8. A gas type identification system comprising:

a flow path;

a temperature measurement section disposed in the flow path;

a temperature calculation section for calculating a temperature of a gas flowing through the flow path based on a signal from the temperature measurement section;

an ultrasonic measurement section disposed in the flow path, the ultrasonic measurement section including a pair of ultrasonic transducers;

a flow rate calculation section for calculating a flow rate of a gas flowing through the flow path based on a signal from the ultrasonic measurement section;

a sound velocity calculation section for calculating a sound velocity of the gas flowing through the flow path based on a signal from the ultrasonic measurement section;

a temperature/sound velocity memory section for previously storing a relationship between gas types, predetermined temperatures and predetermined sound velocities;

a comparison section for comparing the temperature calculated by the temperature calculation section with at least one of the predetermined temperatures in the relationship previously stored in the temperature/sound velocity memory section, for comparing the sound velocity calculated by the sound velocity calculation section with at least one of the predetermined sound velocities in the relationship previously stored in the temperature/sound velocity memory section and for identifying a gas type of the gas flowing through the flow path in accordance with a result of the comparison;

a dual mode valve disposed upstream from the ultrasonic measurement section in the flow path; and a control section for controlling the dual mode valve in accordance with the result of the comparison by the comparison section.

9. A gas type identification system comprising:

a flow path;

a temperature measurement section disposed in the flow path to measure a first temperature and a second temperature of a gas flowing through the flow path;

a temperature calculation section for calculating a temperature of a gas flowing through the flow path based on a signal from the temperature measurement section;

an ultrasonic measurement section disposed in the flow path, the ultrasonic measurement section including a pair of ultrasonic transducers to measure a first sound velocity and a second sound velocity of the gas flowing through the flow path;

a sound velocity calculation section for calculating a sound velocity of a gas flowing through the flow path based on a signal from the ultrasonic measurement section;

a temperature/sound velocity memory section for previously storing a predetermined temperature and a predetermined sound velocity; and a comparison section for comparing the first temperature and the second temperature calculated by the temperature calculation section with the predetermined temperature previously stored in the temperature/sound velocity memory section and comparing the first sound velocity and the second sound velocity calculated by the sound velocity calculation section with the predetermined sound velocity previously stored in the temperature/sound velocity memory section.

10. A gas type identification system according to claim 9, wherein the gas type identification system further comprises:

a flow rate compensation coefficient setting section for setting a flow rate compensation coefficient in accordance with a result of the comparison by the comparison section; and a flow rate calculation section for calculating a flow rate of the gas flowing through the flow path based on the signal from the ultrasonic measurement section and the flow rate compensation coefficient.

11. A gas type identification system according to claim 9, wherein the gas type identification system further comprises:

a dual mode valve disposed in the flow path; and a control section for controlling the dual mode valve in accordance with a result of the determination by the determination section.

12. A gas type identification system according to claim 9, wherein the gas type identification system further comprises:

a dual mode valve disposed in the flow path;

a safety standards setting section for setting safety standards in accordance with a result of the comparison by the comparison section;

a determination section for determining whether or not the safety standards are satisfied; and a control section for controlling the dual mode valve in accordance with a result of the determination by the determination section.

13. A flow rate measurement device comprising:

a flow path;

an ultrasonic measurement section disposed in the flow path, the ultrasonic measurement section including a pair of ultrasonic transducers;

a flow rate calculation section for calculating a flow rate of a gas flowing through the flow path based on a signal from the ultrasonic measurement section;

a sound velocity calculation section for calculating a sound velocity of a gas flowing through the flow path based on a signal from the ultrasonic measurement section;

a sound velocity memory section for previously storing a predetermined sound velocity; and a comparison section for comparing the sound velocity calculated by the sound velocity calculation section with the predetermined sound velocity previously stored in the sound velocity memory section;

wherein a temperature of the gas in inferred based on the sound velocity of the gas calculated by the sound velocity calculation section, and the flow rate of the gas calculated by the flow rate calculation section is compensated based on the inferred temperature.

14. A flow rate measurement device according to claim 13, further comprising a pressure sensor disposed in the flow path, wherein a mass flow rate of the gas is calculated by pressure compensation of the flow rate of the gas.

15. A gas type identification system comprising:

a flow path;

an ultrasonic measurement section disposed in the flow path, the ultrasonic measurement section including a pair of ultrasonic transducers;

a sound velocity calculation section for calculating a sound velocity of a gas flowing through the flow path based on a signal from the ultrasonic measurement section;

a sound velocity memory section for previously storing a predetermined sound velocity; and a comparison section for comparing the sound velocity calculated by the sound velocity calculation section with the predetermined sound velocity previously stored in the sound velocity memory section, wherein the system further comprises:

a dual mode valve disposed in the flow path;

a safety standards setting section for setting safety standards in accordance with a result of the comparison by the comparison section;

a determination section for determining whether or not the safety standards are satisfied; and a control section for controlling the dual mode valve in accordance with a result of the determination by the determination section.

16. A gas type identification system comprising:

a flow path;

a temperature measurement section disposed in the flow path;

a temperature calculation section for calculating a temperature of a gas flowing through the flow path based on a signal from the temperature measurement section;

an ultrasonic measurement section disposed in the flow path, the ultrasonic measurement section including a pair of ultrasonic transducers;

a sound velocity calculation section for calculating a sound velocity of a gas flowing through the flow path based on a signal from the ultrasonic measurement section;

a temperature/sound velocity memory section for previously storing a predetermined temperature and a predetermined sound velocity; and a comparison section for comparing the temperature calculated by the temperature calculation section with the predetermined temperature previously stored in the temperature/sound velocity memory section and comparing the sound velocity calculated by the sound velocity calculation section with the predetermined sound velocity previously stored in the temperature/sound velocity memory section, wherein the system further comprises:

a dual mode valve disposed in the flow path;

a safety standards setting section for setting safety standards in accordance with a result of the comparison by the comparison section;

a determination section for determining whether or not the safety standards are satisfied; and a control section for controlling the dual mode valve in accordance with a result of the determination by the determination section.

* * * * *